United States Patent
Lee et al.

(10) Patent No.: US 8,975,366 B2
(45) Date of Patent: Mar. 10, 2015

(54) ORGANIC SEMICONDUCTOR COMPOUND AND ORGANIC THIN FILM INCLUDING THE ORGANIC SEMICONDUCTOR COMPOUND

(71) Applicant: Samsung Electronics Co., Ltd., Suwon-Si, Gyeonggi-Do (KR)

(72) Inventors: Bang Lin Lee, Suwon-si (KR); Jeong Il Park, Seongnam-si (KR); Jong Won Chung, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/077,888

(22) Filed: Nov. 12, 2013

(65) Prior Publication Data

US 2014/0073754 A1 Mar. 13, 2014

Related U.S. Application Data

(62) Division of application No. 13/479,036, filed on May 23, 2012, now Pat. No. 8,609,803.

(30) Foreign Application Priority Data

Nov. 25, 2011 (KR) ........................ 10-2011-0124609

(51) Int. Cl.
| | | |
|---|---|---|
| *C08G 75/00* | (2006.01) | |
| *H01L 51/00* | (2006.01) | |
| *C07D 417/14* | (2006.01) | |
| *C08G 75/32* | (2006.01) | |
| *C07D 421/14* | (2006.01) | |

(52) U.S. Cl.
CPC .......... *H01L 51/0036* (2013.01); *C07D 417/14* (2013.01); *C08G 75/32* (2013.01); *H01L 51/0043* (2013.01); *H01L 51/0069* (2013.01); *H01L 51/0074* (2013.01); *C07D 421/14* (2013.01)
USPC ............................. 528/377; 528/370; 528/380

(58) Field of Classification Search
CPC ............................................... C08G 2261/3243
USPC .......................................... 528/370, 377, 380
See application file for complete search history.

(56) References Cited

U.S. PATENT DOCUMENTS

| | | | |
|---|---|---|---|
| 6,166,172 A | 12/2000 | McCullough et al. | |
| 8,609,803 B2 | 12/2013 | Lee et al. | |
| 2005/0082525 A1 | 4/2005 | Heeney et al. | |
| 2011/0001131 A1* | 1/2011 | Lee et al. | 257/40 |

FOREIGN PATENT DOCUMENTS

| | | | |
|---|---|---|---|
| JP | 2007-088222 A | 4/2007 | |
| JP | 2010-238880 A | 10/2010 | |

OTHER PUBLICATIONS

Yang et al. J. Phys. Chem. C, 2010, 114, 17989-17994.*

(Continued)

*Primary Examiner* — Shane Fang
(74) *Attorney, Agent, or Firm* — Harness, Dickey, & Pierce, P.L.C.

(57) ABSTRACT

An organic semiconductor compound may be represented by the above Chemical Formula 1 or Chemical Formula 2, and an organic thin film may include the organic semiconductor compound according to Chemical Formula 1 or 2.

7 Claims, 4 Drawing Sheets

(56) References Cited

OTHER PUBLICATIONS

Slocum, D. W. and Giefzer, P. L., "Directed Metalation Reactions.8. Directed Metalation of 3-Mono- and 2,5-Disubstituted Thiophenes", J. Org. Chem., vol. 41, No. 23, pp. 3668-3673, 1976.

Koβmehl, G. et al., "Über Polyarylenalkenylene and Polyheteroarylenalkenylene, 14[a])", Makromol. Chem., vol. 184, pp. 627-650, 1983.

Hou, J. et al., "Bandgap and Molecular Energy Level Control of Conjugated Polymer Photovoltaic Materials Based on Benzo[1,2-b:4,5-b']dithiophene", Macromolecules 2008, vol. 41, pp. 6012-6018.

Dondoni, A. et al., "Synthesis of Stannylthiazoles and Mixed Stannylsilylthiazoles and their Use for a Convenient Preparation of Mono- and Bis-halothiazoles", Synthesis, Sep. 1986, pp. 757-759.

Pan, H. et al., "Low-Temperature, Solution-Processed, High-Mobility Polymer Semiconductors for Thin-Film Transistors", J. Am. Chem. Soc., 2007, vol. 129, pp. 4112-4113.

Milstein, D. and Stille, J. K., "A General, Selective, and Facile Method for Ketone Synthesis from Acid Chlorides and Organotin Compounds Catalyzed by Palladium", Journal of the American Chemical Society, vol. 100:11, May 24, 1978, pp. 3636-3638.

Farina, V. and Krishna, B., "Large Rate Accelerations in the Stifle Reaction with Tri-2-furylohosphine and Triphenylarsine as Palladium Ligands: Mechanistic and Synthetic Implications", J. Am. Chem. Soc., 1991, vol. 113, pp. 9585-9595.

Yamamoto, T. et al., "Preparation of π-Conjugated Poly(thiophene-2,5-diyl), Poly(p-phenylene), and Related Polymers Using Zerovalent Nickel Complexes. Linear Structure and Properties of the π-Conjugated Polymers", Macromolecules, 1992, vol. 25, pp. 1214-1223.

Van Pham, C. et al., "Lithiation Reaction of 2,5-Dibromothiophene. $^{13}$C NMR Spectra of 3-Substituted Derivatives", J. Org. Chem., 1984, vol. 49, pp. 5250-5253.

Stille, J., "The Palladium-Catalyzed Cross-Coupling Reactions of Organotin Reagents with Organic Electrophiles", Angew. Chem. Int. Ed. Engl., vol. 25, 1986, pp. 508-524.

Miyaura, N. et al., "Palladium-Catalyzed Inter- and Intramolecular Cross-Coupling Reactions of B-Alkyl-9borabicyclo[3.3.1]nonane Derivatives with 1-Halo-1-alkenes or Haloarenes. Syntheses of Functionalized Alkenes, Arenes, and Cycloalkenes via Hydroboration-Coupling Sequence", J. Am. Chem. Soc., 1989, vol. 111, pp. 314-321.

Office Action issued in corresponding U.S. Appl. No. 13/736,399 on Apr. 22, 2014.

\* cited by examiner

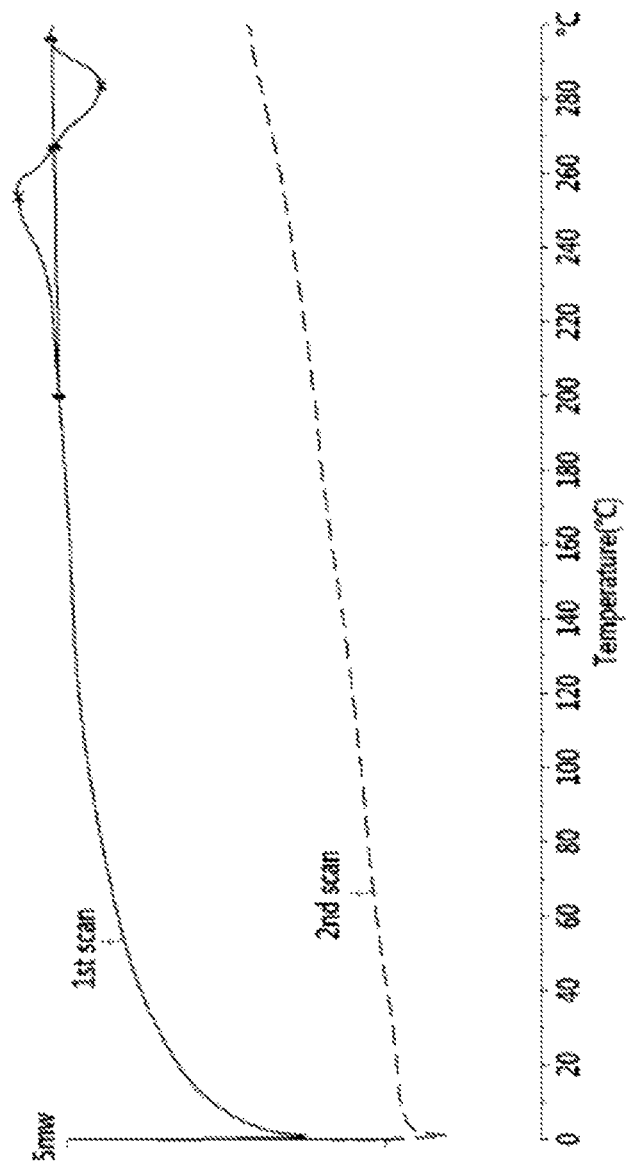

ORGANIC SEMICONDUCTOR COMPOUND AND ORGANIC THIN FILM INCLUDING THE ORGANIC SEMICONDUCTOR COMPOUND

CROSS-REFERENCE TO RELATED APPLICATION

This application is a divisional application of U.S. application Ser. No. 13/479,036, filed on May 23, 2012, which claims priority under 37 U.S.C. §119 to Korean Patent Application No. 10-2011-0124609 filed in the Korean Intellectual Property Office on Nov. 25, 2011, the entire contents of each of which are incorporated herein by reference.

BACKGROUND

1. Field

Example embodiments relate to an organic semiconductor compound and an organic thin film including the same.

2. Description of the Related Art

Progressing to an information-oriented society requires developing a new image display device that addresses the drawbacks of the conventional cathode ray tube (CRT) (including heavy weight and/or larger volume). Several flat panel displays (e.g., a liquid crystal display (LCD), an organic light emitting diode (OLED) display, a plasma display panel (PDP), a surface-conduction electron-emitter display (SED), and similar devices) are drawing attention.

A thin film transistor (TFT) including a semiconductor layer of amorphous silicon is widely used for a switching device of the flat panel displays. The amorphous silicon thin film transistor (TFT) is widely used because the amorphous Si TFT exhibits uniformity and increased electrical characteristics in a doping state, while retaining insulating characteristics in a non-doping state.

However, in order to deposit the conventional amorphous silicon thin film transistor on a substrate, there are limits in carrying out the process at a higher temperature of about 300° C. Applying the conventional amorphous silicon thin film transistor to a polymer substrate used to form a flexible display may be difficult.

In order to solve the problems, an organic thin film transistor (OTFT) using an organic semiconductor material has been suggested. The organic thin film transistor may include a substrate, a gate electrode, an insulation layer, a source electrode, a drain electrode, and a channel region. The organic thin film transistor may be classified as a bottom contact (BC) type having a channel region formed on the source electrode and the drain electrode or a top contact (TC) type having a metal electrode formed on the channel region due to mask deposition.

A low molecular or oligomer organic semiconductor material filled in the channel region of the organic thin film transistor (OTFT) may include merocyanine, phthalocyanine, perylene, pentacene, $C_{60}$, a thiophene oligomer, and similar compounds. The low molecular, or oligomer, organic semiconductor material may be a thin film formed on the channel region according to a vacuum process.

Organic semiconductor compound materials have workability in that large-area processing is possible using a solution method, e.g., printing techniques, at a lower cost.

SUMMARY

Example embodiments provide an organic semiconductor compound having a relatively low bandgap, increased charge mobility, and being capable of being applied to a solution process. Example embodiments also provide an organic thin film including the organic semiconductor compound.

According to example embodiments, an organic semiconductor compound may be represented by the following Chemical Formula 1.

[Chemical Formula 1]

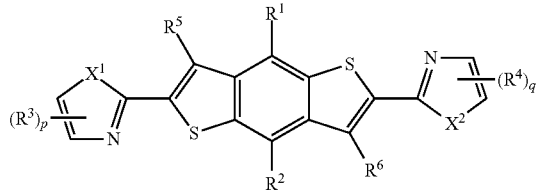

In Chemical Formula 1,
each of $X^1$ and $X^2$ are independently one of S, Se, and $NR^a$ (wherein $R^a$ is selected from hydrogen, a substituted or unsubstituted $C_1$ to $C_{30}$ linear or branched alkyl group, a substituted or unsubstituted $C_3$ to $C_{30}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group), each of $R^1$ to $R^4$ are independently one of a halogen (—F, —Cl, —Br, or —I), a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, a substituted or unsubstituted $C_2$ to $C_{30}$ heteroaryl group, —$COR^b$ (wherein $R^b$ is selected from a substituted or unsubstituted $C_1$ to $C_{20}$ linear or branched alkyl group, a substituted or unsubstituted $C_3$ to $C_{30}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group) and —$C(=O)OR^c$ (wherein $R^c$ is selected from hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group), each of $R^5$ and $R^6$ are independently one of hydrogen and a $C_1$ to $C_{10}$ alkyl group, and each of p and q are an integer of 1 or 2.

According to example embodiments, an organic semiconductor compound may include a structural unit represented by the following Chemical Formula 2.

[Chemical Formula 2]

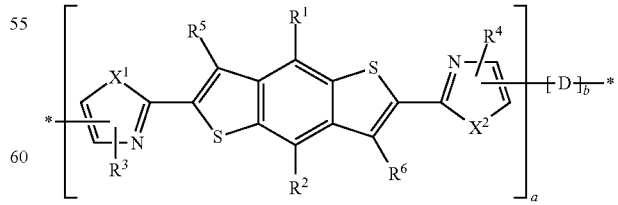

In Chemical Formula 2
$X^1$, $X^2$ and $R^1$ to $R^5$ are the same as in Chemical Formula 1,
-D- is one of a substituted or unsubstituted $C_1$ to $C_{20}$ alkylene group, a substituted or unsubstituted $C_4$ to $C_{20}$ aromatic ring, a substituted or unsubstituted $C_4$ to $C_{14}$ heteroaromatic ring, and a substituted or unsubstituted $C_6$ to $C_{30}$ condensed polycyclic group including a heteroaromatic ring, and a and b represent a mole ratio of each structural unit, wherein a ranges from about 1 mol % to about 100 mol %, and b ranges from about 0 mol % to about 99 mol %, based on a sum, 100 mol % of a and b.

The -D- structural unit may be one of the structural units represented by the following Chemical Formula 3.

[Chemical Formula 3]

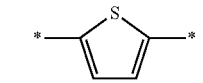 (1)

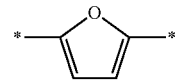 (2)

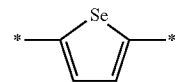 (3)

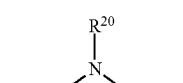 (4)

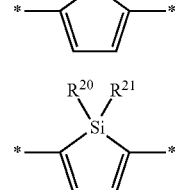 (5)

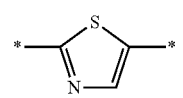 (6)

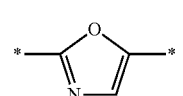 (7)

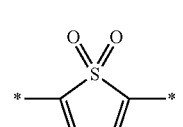 (8)

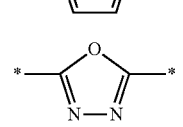 (9)

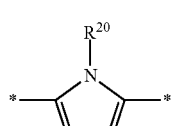 (10)

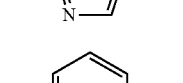 (11)

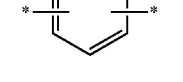 (12)

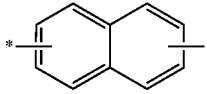 (12)

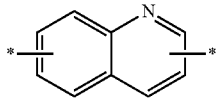 (13)

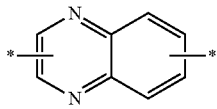 (14)

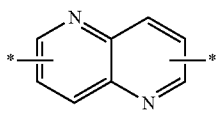 (15)

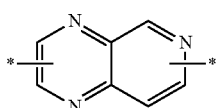 (16)

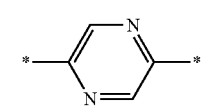 (17)

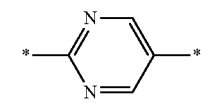 (18)

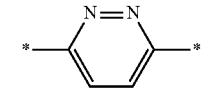 (19)

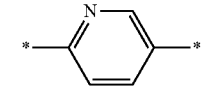 (20)

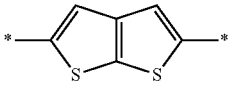 (21)

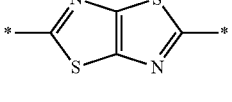 (22)

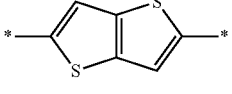 (23)

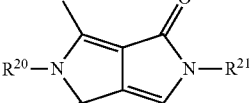 (24)

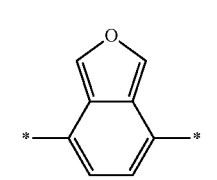 (25)

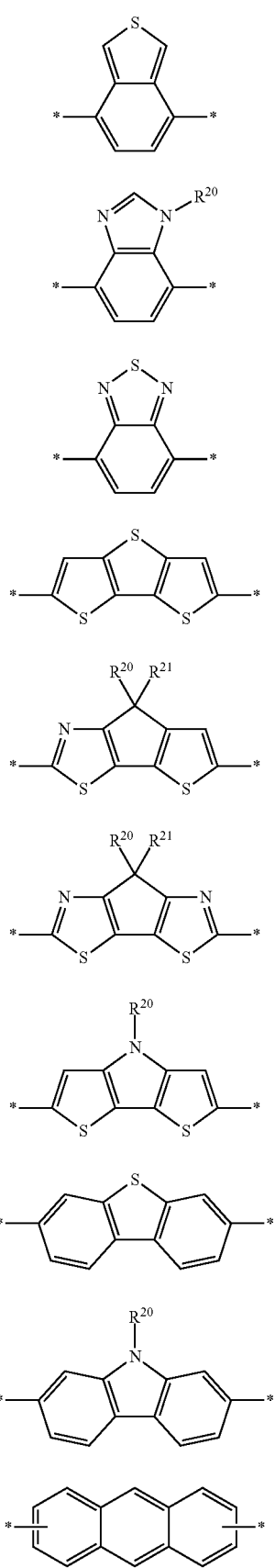
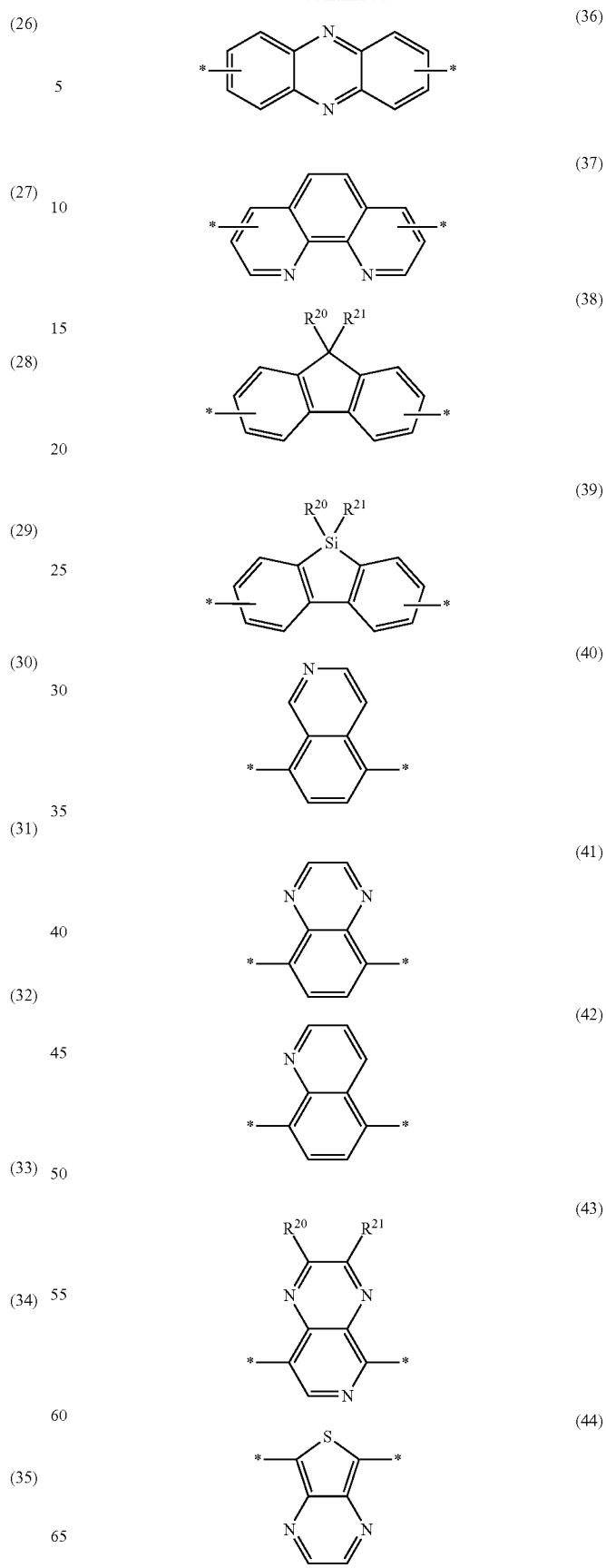

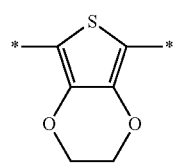 (45)
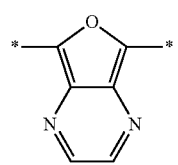 (46)
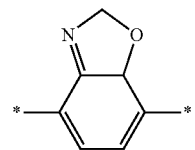 (47)
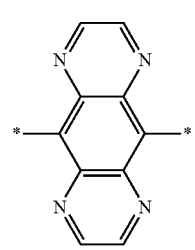 (48)
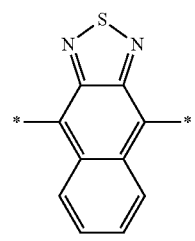 (49)
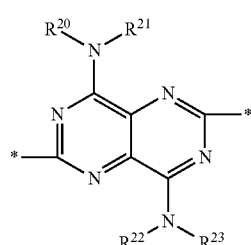 (50)
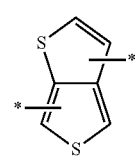 (51)
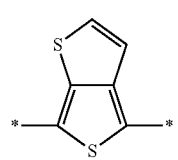 (52)
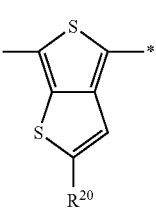 (53)
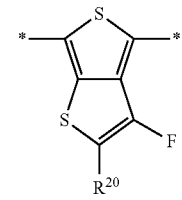 (54)
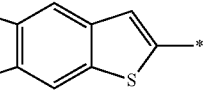 (55)
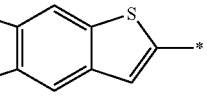 (56)
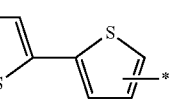 (57)
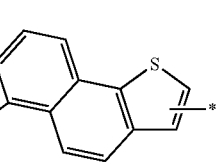 (58)
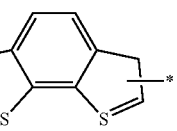 (59)
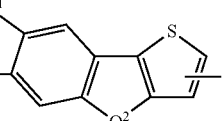 (60)
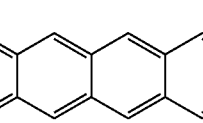 (61)
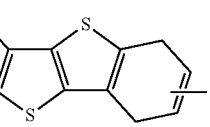 (62)
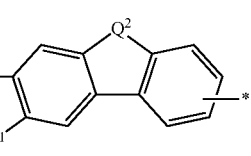 (63)

-continued

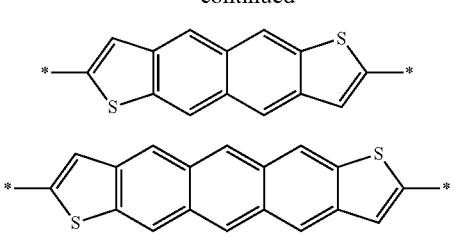

In Chemical Formula 3, each of $R^{20}$ to $R^{23}$ are independently one of a hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, a substituted or unsubstituted $C_2$ to $C_{30}$ heteroaryl group, and a combination thereof, and each of $Q^1$ and $Q^2$ are independently one of S, $CR^{24}R^{25}$, $NR^{26}$, or $SiR^{27}R^{28}$, wherein each of $R^{24}$ to $R^{28}$ are independently hydrogen, a substituted or unsubstituted $C_1$ to $C_{15}$ linear or branched alkyl group, a substituted or unsubstituted $C_3$ to $C_{15}$ cycloalkyl group, a substituted or unsubstituted $C_1$ to $C_{15}$ alkoxy group, a substituted or unsubstituted $C_6$ to $C_{15}$ aryl group, a substituted or unsubstituted $C_2$ to $C_{15}$ heteroaryl group, and a combination thereof.

A hydrogen of —CH— or —CH$_2$— positioned in the aromatic ring or heteroaromatic ring of the above Chemical Formula 3 may be optionally substituted with one selected from a fluoro group, a $C_1$ to $C_{10}$ fluoroalkyl group, a $C_1$ to $C_{20}$ linear or branched alkyl group, a $C_3$ to $C_{20}$ cycloalkyl group, a $C_1$ to $C_{20}$ alkoxy group, a substituted or unsubstituted $C_6$ to $C_{30}$ aryl group, and a substituted or unsubstituted $C_2$ to $C_{30}$ heteroaryl group.

The -D- structural unit may be a structural unit represented by the following Chemical Formula 4 including a substituted or unsubstituted thiophene structural unit.

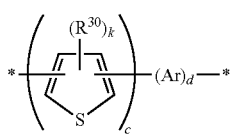

[Chemical Formula 4]

In Chemical Formula 4, $R^{30}$ is selected from one of hydrogen, a substituted or unsubstituted $C_4$ to $C_{20}$ aromatic ring, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group, k is an integer of 1 or 2, -Ar- is one of a substituted or unsubstituted $C_4$ to $C_{20}$ aromatic ring, a substituted or unsubstituted $C_4$ to $C_{14}$ heteroaromatic ring, and a substituted or unsubstituted $C_6$ to $C_{30}$ condensed polycyclic group including a heteroaromatic ring, and c and d represent a mole ratio of each structural unit, wherein c ranges from about 1 mol % to about 99 mol %, and d ranges from about 1 mol % to from about 99 mol % based on a sum, 100 mol % of c and d.

The -Ar- of the Chemical Formula 4 may be one of the above structural units represented by Chemical Formula 3.

The organic semiconductor compound represented by Chemical Formula 1 or Chemical Formula 2 may include one of terminal functional groups represented by the following Chemical Formulas 5 to 8.

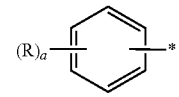

[Chemical Formula 5]

In Chemical Formula 5, R is one of a fluoro group and a $C_1$ to $C_{20}$ perfluoroalkyl group, and a is an integer ranging from 1 to 5.

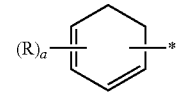

[Chemical Formula 6]

In Chemical Formula 6, R is one of a fluoro group and a $C_1$ to $C_{20}$ perfluoroalkyl group, and a is an integer ranging from 1 to 6.

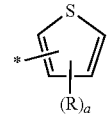

[Chemical Formula 7]

In Chemical Formula 7, R is one of a fluoro group and a $C_1$ to $C_{20}$ perfluoroalkyl group, and a is an integer ranging from 1 to 3.

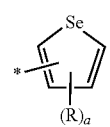

[Chemical Formula 8]

In Chemical Formula 8, R is one of a fluoro group and a $C_1$ to $C_{20}$ perfluoroalkyl group, and a is an integer ranging from 1 to 3.

The organic semiconductor compound represented by Chemical Formula 1 may include organic semiconductor compounds represented by the following Chemical Formula 9, and the organic semiconductor compound represented by Chemical Formula 2 may include organic semiconductor compounds including one of structural units represented by the following Chemical Formula 10.

[Chemical Formula 9]

(9-1)
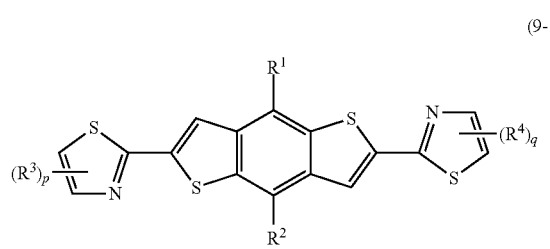

(9-2)
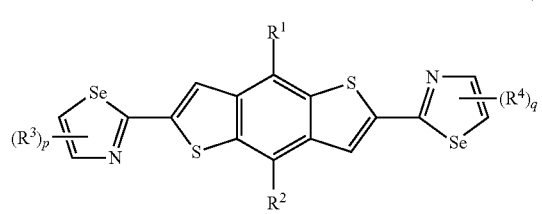

(9-3)
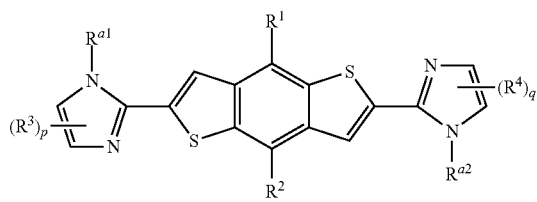

In Chemical Formula 9, $R^1$ to $R^4$ are the same as in Chemical Formula 1, $R^{a1}$ to $R^{a2}$ are selected from one of hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group, and p and q are integers of 1 or 2.

[Chemical Formula 10]

(10-1)
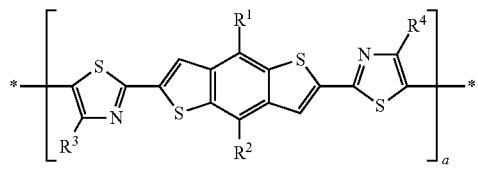

(10-2)
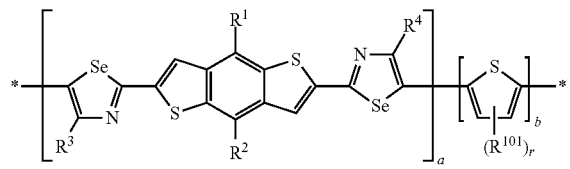

(10-3)
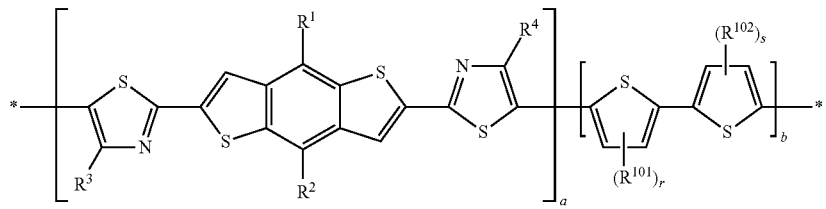

(10-4)
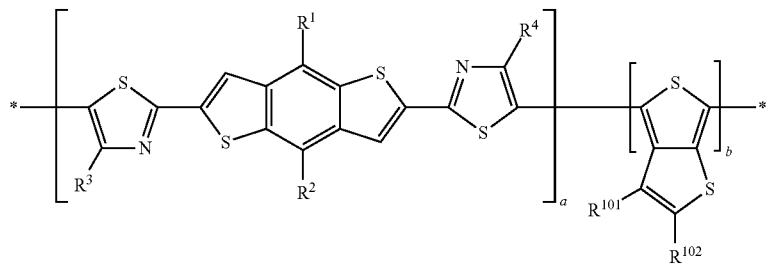

(10-5)
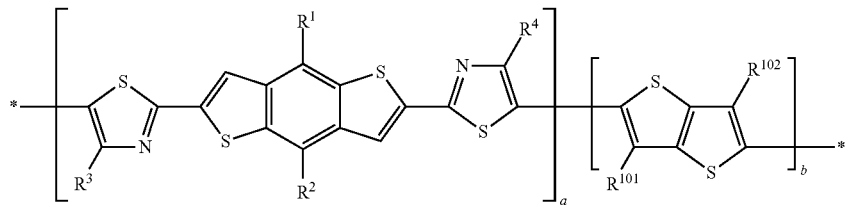

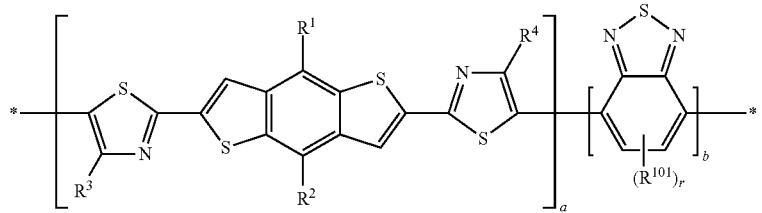
(10-6)
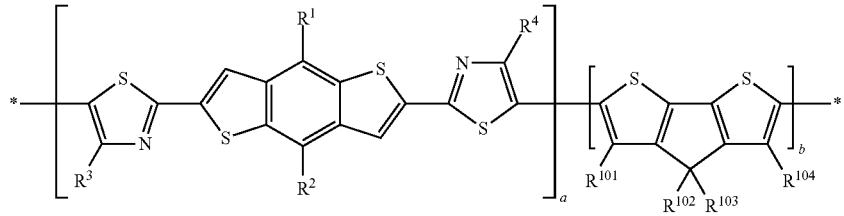
(10-7)
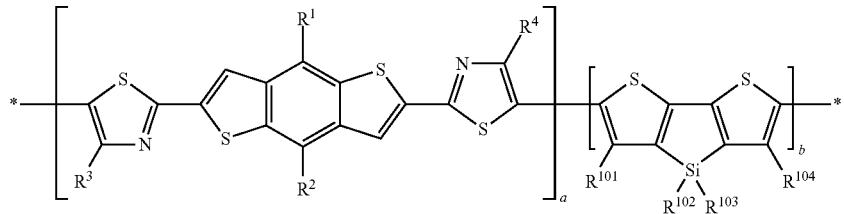
(10-8)
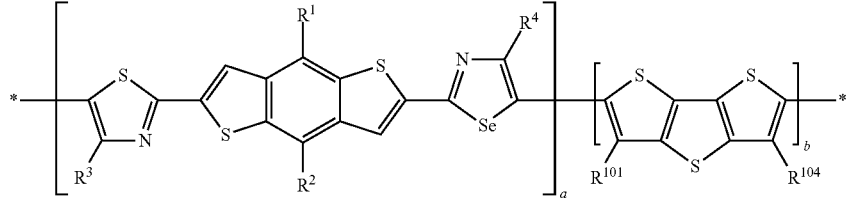
(10-9)
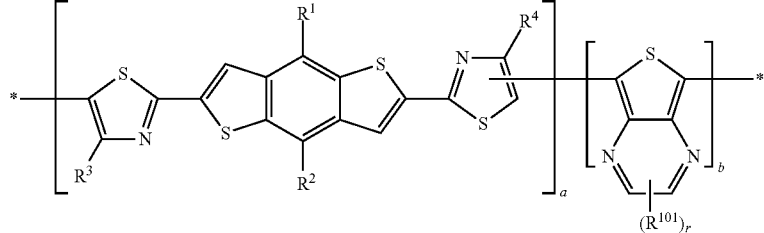
(10-10)
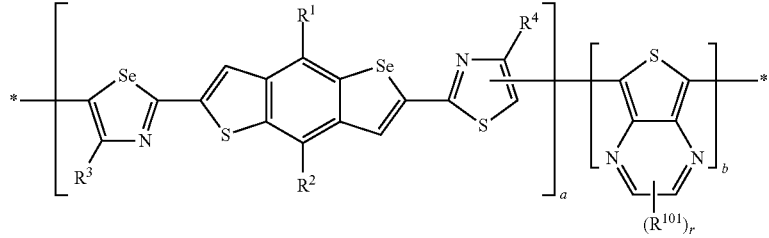
(10-11)

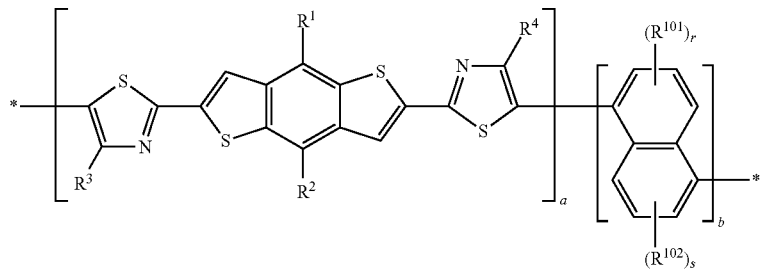

(10-12)

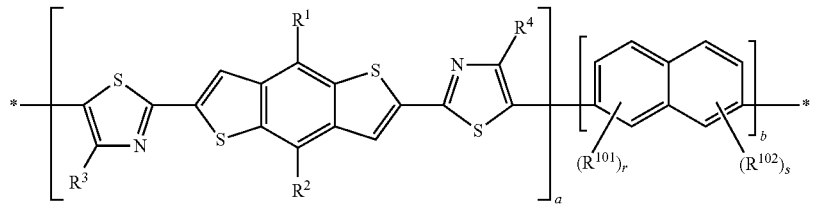

(10-13)

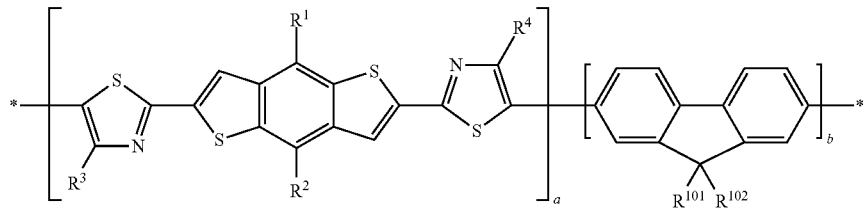

(10-14)

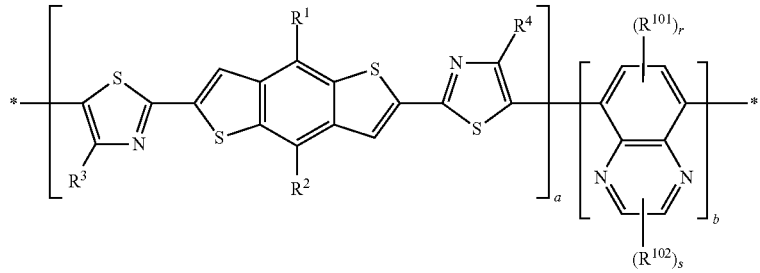

(10-15)

In Chemical Formula 10, $R^1$ to $R^4$ are the same as in Chemical Formula 1, each of $R^{101}$ and $R^{102}$ are independently selected from one of hydrogen, a substituted or unsubstituted $C_4$ to $C_{20}$ aromatic ring, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group, r and s are integers of 1 or 2, and a and b represent a mole ratio of each structural unit, wherein a ranges from about 1 mol % to about 100 mol %, and b ranges from about 0 mol % to about 99 mol %, based on a sum, 100 mol % of a and b.

According to example embodiments, an organic thin film may include the organic semiconductor compound selected from the organic semiconductor compound represented by Chemical Formula 1, the organic semiconductor compound represented by Chemical Formula 2, and a combination thereof.

BRIEF DESCRIPTION OF THE DRAWINGS

Example embodiments will be more clearly understood from the following brief description taken in conjunction with the accompanying drawings. FIGS. 1 to 4 represent non-limiting, example embodiments as described herein.

FIG. 1 shows a 1H-NMR spectrum of the organic semiconductor compound (7) according to Example 1.

FIG. 2 shows a 1H-NMR spectrum of the organic semiconductor compound (7) according to Example 2.

FIG. 3 shows UV absorption spectra of the organic semiconductor compound II according to Example 6 in a solution state and a film state.

FIG. 4 shows differential scanning calorimetry (DSC) analysis results of the organic semiconductor compound (11) according to Example 6.

DETAILED DESCRIPTION

Figure 1:
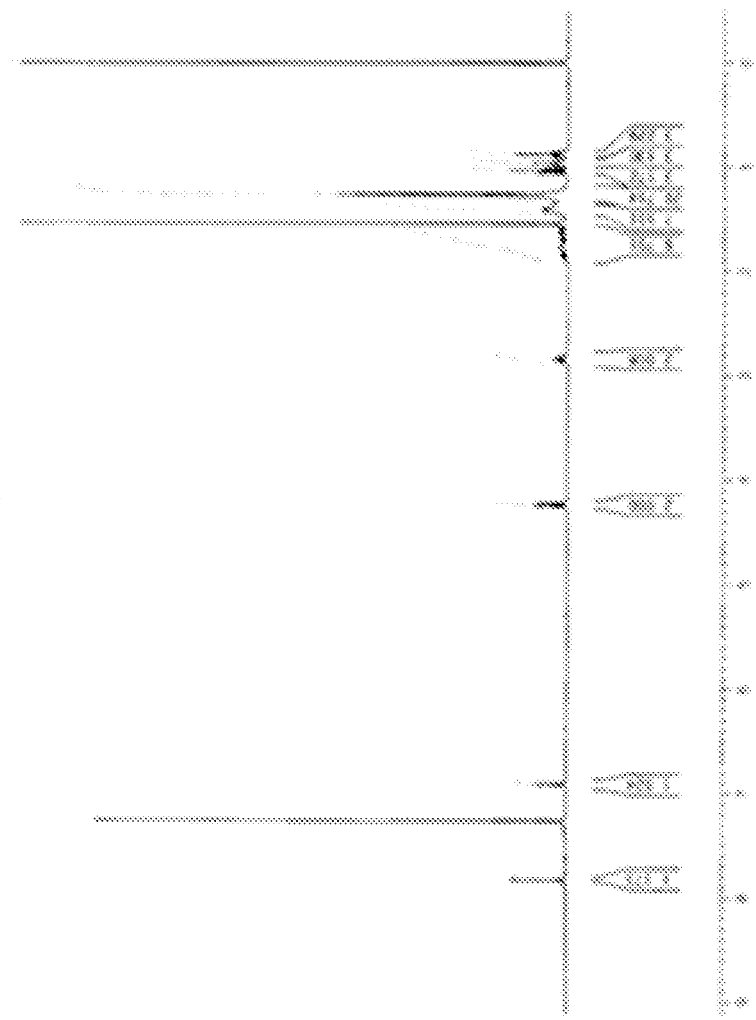

Example embodiments will now be described more fully with reference to the accompanying drawings, in which example embodiments are shown. Example embodiments may, however, be embodied in many different forms and is not to be construed as being limited to the embodiments set forth herein; rather, these embodiments are provided so that this disclosure will be thorough and complete, and will fully convey the concept of example embodiments to those of ordinary skill in the art. In the drawings, the thicknesses of layers and regions are exaggerated for clarity. Like reference numerals in the drawings denote like elements, and thus their description will be omitted.

It will be understood that, although the terms "first", "second", etc. may be used herein to describe various elements, components, regions, layers and/or sections, these elements, components, regions, layers and/or sections are not to be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments are not to be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, is to be interpreted as having a meaning that is consistent with their meaning in the context of the relevant art and will not be interpreted in an idealized or overly formal sense unless expressly so defined herein.

As used herein, the term "combination thereof" refers to a mixture, a stacked structure, a composite, an alloy, or the like.

As used herein, when a definition is not otherwise provided, the term "hetero" may refer to one including 1 to 4 heteroatoms selected from N, O, S, Se, Si, and P and remaining carbons. The total number of ring members may be 3 to 10. If multiple rings are present, each ring is independently aromatic, saturated, or partially unsaturated, and multiple rings, if present, may be fused, pendant, spirocyclic, or a combination thereof. The term "heterocycloalkyl group" may be at least one non-aromatic ring including a heteroatom, and the term "heteroaryl group" may be at least one aromatic ring including a heteroatom. Non-aromatic and/or carbocyclic rings may also be present in a heteroaryl group, provided that at least one ring is both aromatic and contains a ring member that is a heteroatom.

As used herein, when a definition is not otherwise provided, the term "alkyl group" may be a linear or branched, saturated, monovalent hydrocarbon group (e.g., a methyl group, an ethyl group, a propyl group, an isobutyl group, a sec-butyl group, a tert-butyl group, a pentyl group, an isoamyl group, a hexyl group, and the like).

The term "alkoxy group" may refer to an alkyl group that is linked via an oxygen, e.g., a methoxy group, an ethoxy group, and a sec-butyloxy group.

The term "aryl group" may refer to a monovalent functional group formed by the removal of one hydrogen atom from one or more rings of an arene, e.g., phenyl or naphthyl. The arene may refer to a hydrocarbon having an aromatic ring, and includes monocyclic and polycyclic hydrocarbons wherein the additional ring(s) of the polycyclic hydrocarbon may be aromatic or nonaromatic.

The term "aryloxy group" may refer to an aryl group that is linked via an oxygen, and the aryl group is the same as described above.

The "arylalkyl group" may refer to an aryl group where at least one hydrogen is substituted with a lower alkylene, e.g., methylene, ethylene, propylene, and the like. For example, the "arylalkyl group" may be a benzyl group or a phenylethyl group.

The term "cycloalkyl group" may refer to a monovalent functional group having one or more saturated rings in which all ring members are carbon, e.g., a cyclopentyl group and a cyclohexyl group.

As used herein, when a definition is not otherwise provided, the term "aromatic ring" refers to a functional group in which all atoms in the cyclic functional group have a p-orbital, wherein these p-orbitals are conjugated. For example, the aromatic ring may be a $C_6$ to $C_{20}$ aryl group.

As used herein, when a definition is not otherwise provided, the term "heteroaromatic ring" may refer to a functional group including 1 to 4 heteroatoms selected from N, O, and S in a ring in which all atoms in the cyclic functional group have a p-orbital, wherein the p-orbital is conjugated. For example, the heteroaromatic ring may refer to a $C_2$ to $C_{30}$ heteroaryl group, a $C_3$ to $C_{30}$ heterocycloalkenyl group, or a $C_3$ to $C_{30}$ heterocycloalkynyl group.

The term "condensed polycyclic group" may refer to a fused ring including the foregoing heteroaromatic ring linked to at least one ring selected from a $C_3$ to $C_{30}$ cycloalkyl group, a $C_3$ to $C_{30}$ cycloalkenyl group, a $C_2$ to $C_{30}$ heterocycloalkyl group, a $C_2$ to $C_{30}$ heteroaryl group, and a $C_3$ to $C_{30}$ heterocycloalkenyl group.

As used herein, when a definition is not otherwise provided, the term "substituted" may mean that a functional group or a compound is substituted with at least one substituent selected independently from a halogen (—F, —Cl, —Br, or —I), a $C_1$ to $C_{30}$ linear or branched alkyl group, for example a $C_1$ to $C_{10}$ linear or branched alkyl group, a $C_2$ to $C_{30}$ linear or branched alkenyl group, for example a $C_2$ to $C_{10}$ linear or branched alkenyl group, a $C_2$ to $C_{30}$ linear or branched alkynyl group, for example a $C_2$ to $C_{10}$ linear or branched alkynyl group, $C_6$ to $C_{30}$ aryl group, for example a $C_6$ to $C_{12}$ aryl group, a $C_2$ to $C_{30}$ heteroaryl group, for example a $C_2$ to $C_{12}$ heteroaryl group, a $C_3$ to $C_{30}$ cycloalkyl group, a $C_1$ to $C_{20}$ fluoroalkyl group, a $C_1$ to $C_{20}$ perfluoroalkyl group ($CnF_{2n+1}$, wherein n is an integer of 1 to 20), a $C_1$ to $C_{30}$ linear or branched alkoxy group, a $C_3$ to $C_{30}$ cycloalkyloxy group, a $C_2$ to $C_{30}$ linear or branched alkoxyalkyl group, a $C_4$ to $C_{30}$ cycloalkyloxyalkyl group, a cyano group, an amino group (—NRR', wherein R and R' are independently one of hydrogen and a $C_1$ to $C_{10}$ alkyl group), an amidino group (—C(=NH)NH_2), a nitro group (—NO_2), an amide group (—C(=O)N(H)R, wherein R is one of hydrogen and a $C_1$ to $C_{10}$ alkyl group), an aldehyde group (—C(=O)H), a hydroxy group (—OH), a sulfonyl group (—S(=O)_2R, wherein R is independently one of hydrogen and a $C_1$ to $C_{10}$ alkyl group), and a carbamate group (—NH_2COOR, wherein R is a $C_1$ to $C_{10}$ alkyl group), instead of hydrogen, provided that the substituted atom's normal valence is not exceeded.

According to example embodiments, an organic semiconductor compound may be represented by the following Chemical Formula 1.

[Chemical Formula 1]

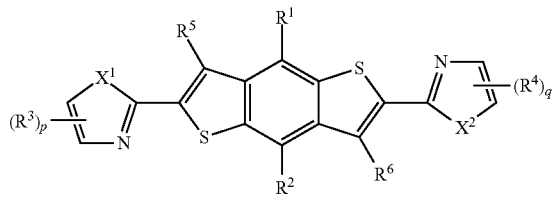

In Chemical Formula 1, each of $X^1$ and $X^2$ are independently one of S, Se, and $NR^a$ (wherein, $R^a$ is selected from hydrogen, a substituted or unsubstituted $C_1$ to $C_{30}$ linear or branched alkyl group, a substituted or unsubstituted $C_3$ to $C_{30}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group).

Each of $R^1$ to $R^4$ are independently selected from one of a halogen (—F, —Cl, —Br, or —I), a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, a substituted or unsubstituted $C_2$ to $C_{30}$ heteroaryl group, —$COR^b$ (wherein $R^b$ is selected from a substituted or unsubstituted $C_1$ to $C_{20}$ linear or branched alkyl group, a substituted or unsubstituted $C_3$ to $C_{30}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group) and —C(=O)$OR^c$ (wherein $R^c$ is selected from hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group).

Each of $R^5$ and $R^6$ are independently one of hydrogen and a $C_1$ to $C_{10}$ alkyl group, and each of p and q are an integer of 1 or 2. When p and q are 2, a plurality of $R^3$ and $R^4$ may be the same or different.

The organic semiconductor compound represented by the above Chemical Formula 1 may have a structure in which functional groups (e.g., one of a thiazolyl group, an oxazolyl group, a selenazolyl group, and an imidazolyl group) having an aromatic ring structure of N-included rings are symmetrically bound at the ends in the center of the benzo[1,2-b:4,5-b']dithiophene structure. The organic semiconductor compound having the structure may have improved coplanarity to provide a condensed film having a stronger intermolecular stacking property. Thereby, the charge mobility between molecules, e.g., intermolecular, may be improved, and the interrupt current may be decreased by adjusting the energy level.

In addition, by introducing a $C_8$ to $C_{30}$ long aliphatic unsaturated hydrocarbon chain group (e.g., a substituted or unsubstituted $C_8$ to $C_{30}$ alkyl group) into at least one of $R^1$ and $R^2$ in Chemical Formula 1, the dissolubility of the organic semiconductor compound in the organic solvent may be improved. The improvement in dissolubility may enable a simpler coating process even by a solution process at room temperature (about 23° C. to about 25° C.) and to provide a thin film having a relatively wide area, which is effective in the view of processibility and workability. When a saturated hydrocarbon chain group is present instead of the unsaturated hydrocarbon chain group, the dissolubility to the solvent may be deteriorated such that the film is hardly formed, and the stability to light may be deteriorated.

In Chemical Formula 1, each of $R^3$ and $R^4$ may independently be one of a thiazolyl group, an oxazolyl group, a selenazolyl group, and an imidazolyl group. Herein, the term "combination thereof" may refer to a group including at least two functional groups selected from the thiazolyl group, oxazolyl group, selenazolyl group, and imidazolyl group that are linked to each other through a single bond. In example embodiments, a conjugation structure is extended, and thus, bandgap energy may be reduced.

According to example embodiments, an organic semiconductor compound may include a structural unit represented by the following Chemical Formula 2 that is obtained by polymerizing the organic semiconductor compound represented by Chemical Formula 1.

[Chemical Formula 2]

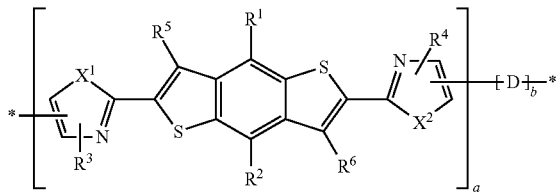

In Chemical Formula 2
$X^1$, $X^2$ and $R^1$ to $R^5$ are the same as in Chemical Formula 1, -D- is one of a substituted or unsubstituted $C_1$ to $C_{20}$ alkylene group, a substituted or unsubstituted $C_4$ to $C_{20}$ aromatic ring, a substituted or unsubstituted $C_4$ to $C_{14}$ heteroaromatic ring, and a substituted or unsubstituted $C_6$ to $C_{30}$ condensed polycyclic group including a heteroaromatic ring, and a and b represent a mole ratio of each structural unit, wherein a ranges from about 1 mol % to about 100 mol %, and b ranges from about 0 mol % to about 99 mol %, based on a sum, 100 mol % of, a and b.

In example embodiments, a may range from about 1 mol % to about 90 mol %, for example, about 1 mol % to about 80 mol %, and b may range from about 10 mol % to about 99 mol, for example, about 20 mol % to about 99 mol %.

The -D- structural unit may be one of the structural units represented by the following Chemical Formula 3.

[Chemical Formula 3]

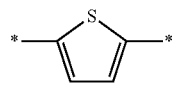 (1)

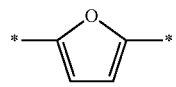 (2)

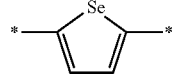 (3)

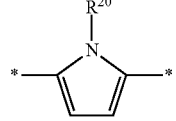 (4)

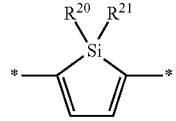 (5)

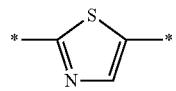 (6)

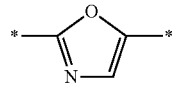 (7)

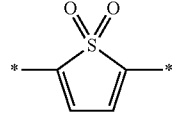 (8)

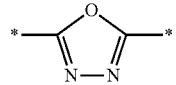 (9)

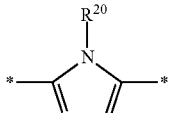 (10)

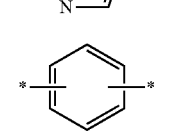 (11)

-continued

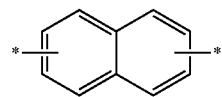 (12)

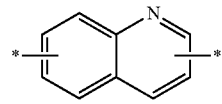 (13)

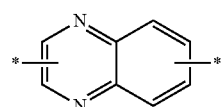 (14)

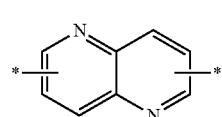 (15)

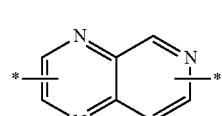 (16)

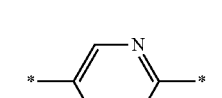 (17)

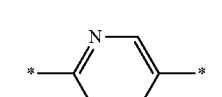 (18)

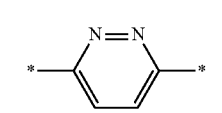 (19)

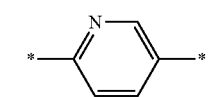 (20)

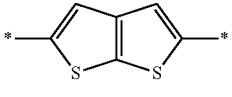 (21)

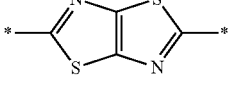 (22)

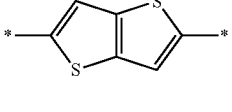 (23)

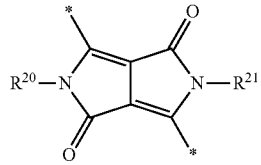 (24)

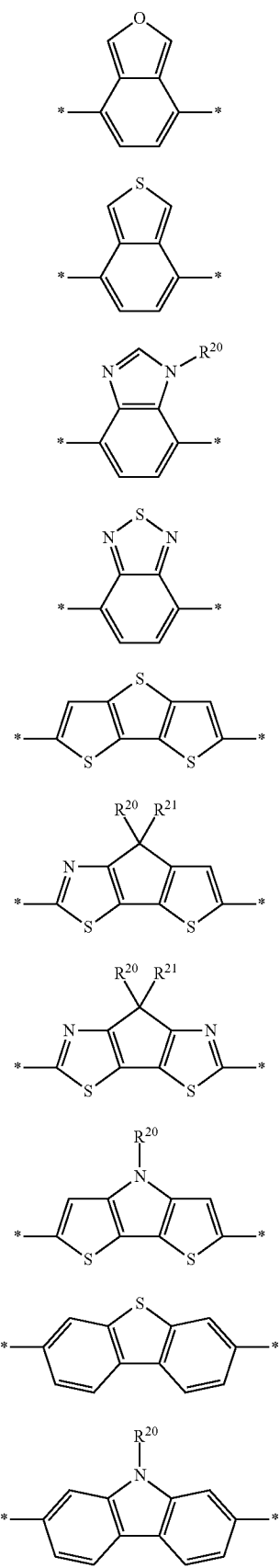
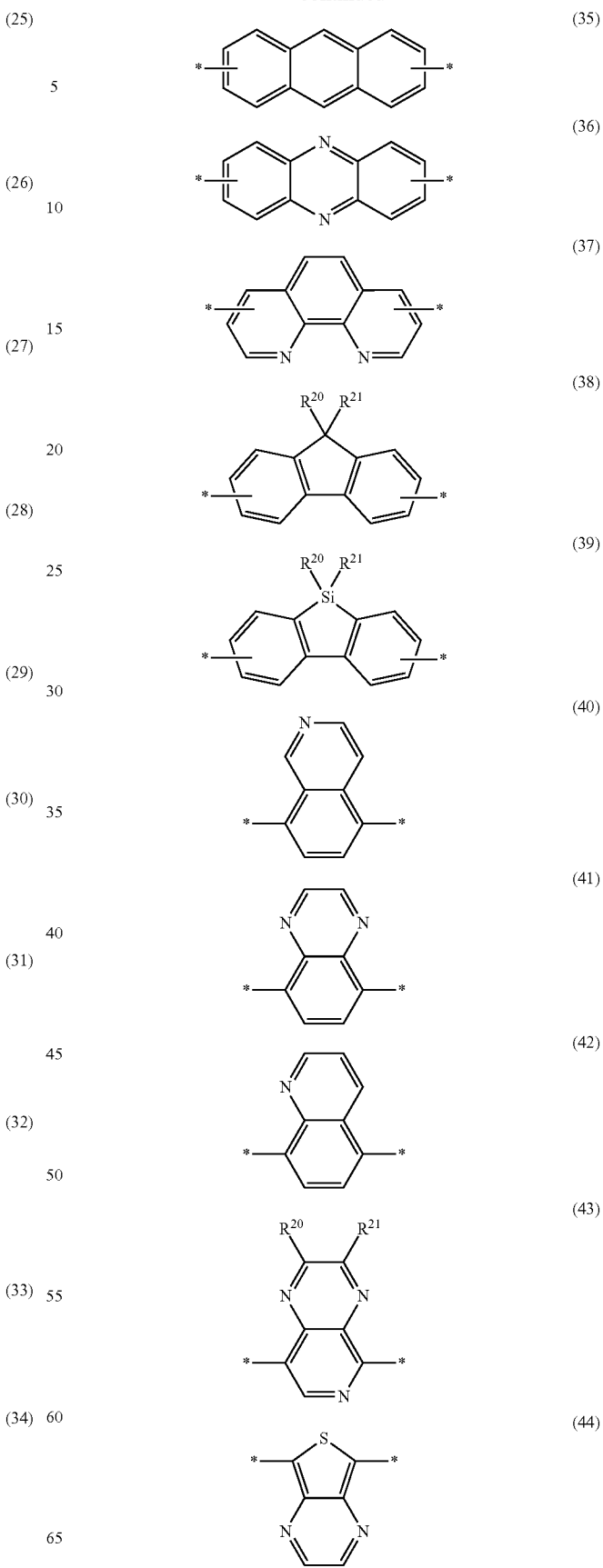

-continued
(45)
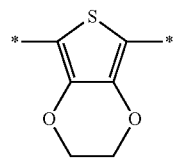
(46)
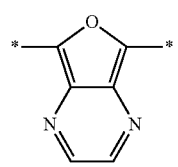
(47)
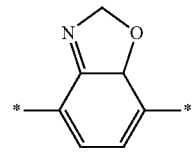
(48)
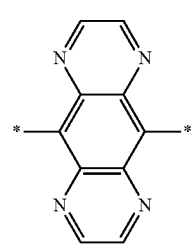
(49)
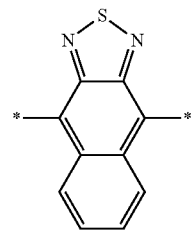
(50)
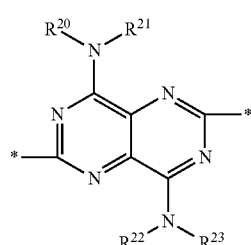
(51)
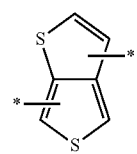
(52)
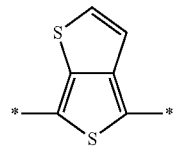
-continued
(53)
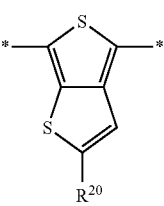
(54)
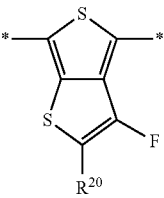
(55)
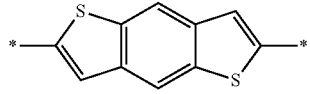
(56)
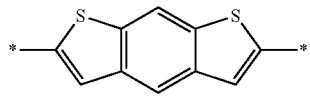
(57)
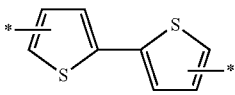
(58)
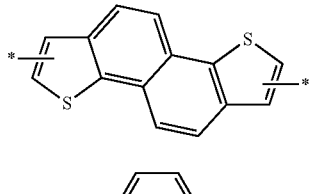
(59)
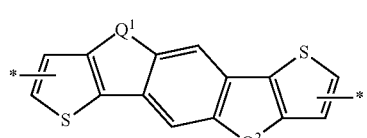
(60)
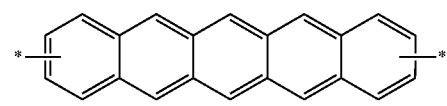
(61)
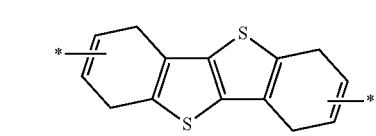
(62)
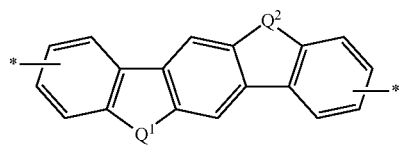
(63)

-continued

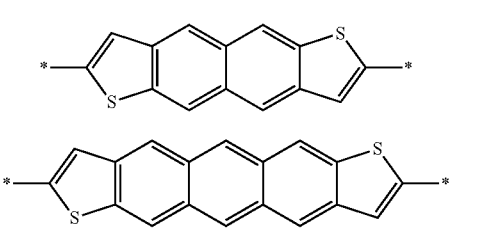

In Chemical Formula 3, each of $R^{20}$ to $R^{23}$ are independently selected from one of hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group.

Each of $Q^1$ and $Q^2$ are independently one of S, $CR^{24}R^{25}$, $NR^{26}$, and $SiR^{27}R^{28}$, wherein each of $R^{24}$ to $R^{28}$ are independently selected from one of hydrogen, a substituted or unsubstituted $C_1$ to $C_{15}$ linear or branched alkyl group, a substituted or unsubstituted $C_3$ to $C_{15}$ cycloalkyl group, a substituted or unsubstituted $C_1$ to $C_{15}$ alkoxy group, a substituted or unsubstituted $C_6$ to $C_{15}$ aryl group, a substituted or unsubstituted $C_2$ to $C_{15}$ heteroaryl group, and a combination thereof, and a hydrogen of —CH— or —CH$_2$— positioned in the aromatic ring or heteroaromatic ring of the above Chemical Formula 3 may be optionally substituted with one selected from a fluoro group, a $C_1$ to $C_{10}$ fluoroalkyl group, a $C_1$ to $C_{20}$ linear or branched alkyl group, a $C_3$ to $C_{20}$ cycloalkyl group, a $C_1$ to $C_{20}$ alkoxy group, a substituted or unsubstituted $C_6$ to $C_{30}$ aryl group, and a substituted or unsubstituted $C_2$ to $C_{30}$ heteroaryl group.

The organic semiconductor compound represented by Chemical Formula 2 may include a first structural unit derived from the organic semiconductor compound represented by the Chemical Formula 1 and a second structural unit represented by -D-. The first structural unit and the second structural unit may be arranged as a block unit, alternately arranged, or randomly arranged.

The second structural unit may be a structural unit represented by the following Chemical Formula 4 including a substituted or unsubstituted thiophene structural unit.

[Chemical Formula 4]

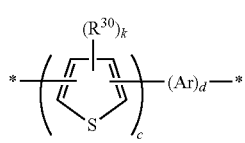

In Chemical Formula 4, $R^{30}$ is selected from hydrogen, a substituted or unsubstituted $C_4$ to $C_{20}$ aromatic ring, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group, and k is an integer of 1 or 2.

-Ar- is one of a substituted or unsubstituted $C_4$ to $C_{20}$ aromatic ring, a substituted or unsubstituted $C_4$ to $C_{14}$ heteroaromatic ring, and a substituted or unsubstituted $C_6$ to $C_{30}$ condensed polycyclic group including a heteroaromatic ring, and c and d represent a mole ratio of each structural unit, wherein c ranges from about 1 mol % to about 99 mol %, and d ranges from about 1 mol % to about 99 mol % based on a sum, 100 mol % of c and d. In example embodiments, c may range from about 1 mol % to about 80 mol %, and d may range from about 20 mol % to about 99 mol %. The -A$_3$- of the Chemical Formula 4 may be one of the above structural units represented by Chemical Formula 3.

In Chemical Formula 4, a substituted or unsubstituted thiophene structural unit and an -Ar- structural unit may be arranged as a block unit, alternately arranged, or randomly arranged.

The organic semiconductor compound of the above Chemical Formula 1 or Chemical Formula 2 may include one of terminal functional groups represented by the following Chemical Formulas 5 to 8.

[Chemical Formula 5]

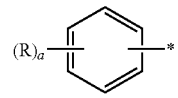

In Chemical Formula 5, R is one of a fluoro group and a $C_1$ to $C_{20}$ perfluoroalkyl group, and a is an integer ranging from 1 to 5.

[Chemical Formula 6]

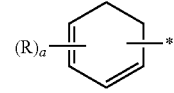

In Chemical Formula 6, R is one of a fluoro group and a $C_1$ to $C_{20}$ perfluoroalkyl group, and a is an integer ranging from 1 to 6.

[Chemical Formula 7]

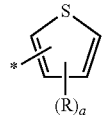

In Chemical Formula 7, R is one of a fluoro group and a $C_1$ to $C_{20}$ perfluoroalkyl group, and a is an integer ranging from 1 to 3.

[Chemical Formula 8]

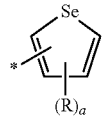

In Chemical Formula 8, R is one of a fluoro group and a $C_1$ to $C_{20}$ perfluoroalkyl group, and a is an integer ranging from 1 to 3.

The organic semiconductor compound represented by Chemical Formula 1 may be organic semiconductor compounds represented by the following Chemical Formula 9.

[Chemical Formula 9]

(9-1)

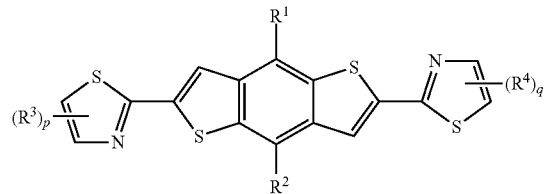

-continued (9-2)

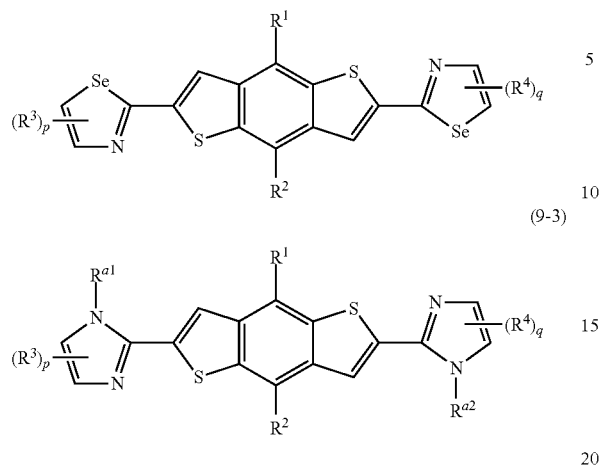

(9-3)

In Chemical Formula 9, $R^1$ to $R^4$ are the same as in Chemical Formula 1, $R^{a1}$ to $R^{a2}$ are selected from hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group, and p and q are integers of 1 or 2.

When p and q are 2, a plurality of $R^3$ and $R^4$ may be the same or different.

For example, the organic semiconductor compound represented by Chemical Formula 1 may be organic semiconductor compounds represented by the following Chemical Formula 9A.

[Chemical Formula 9A]

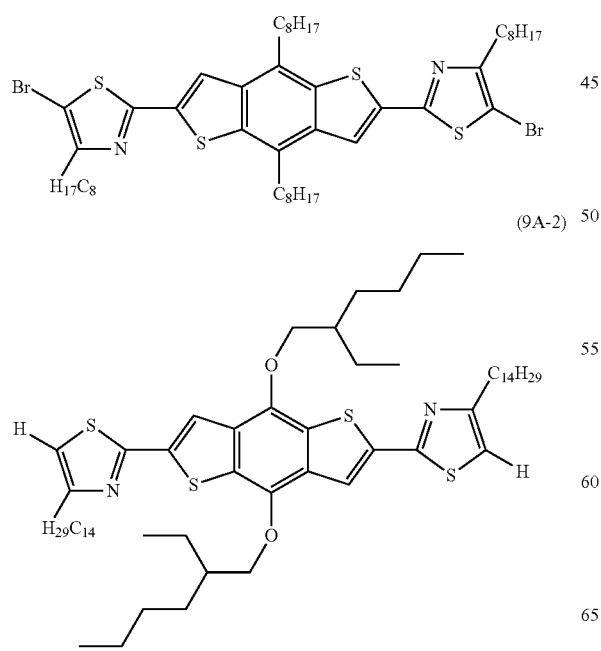

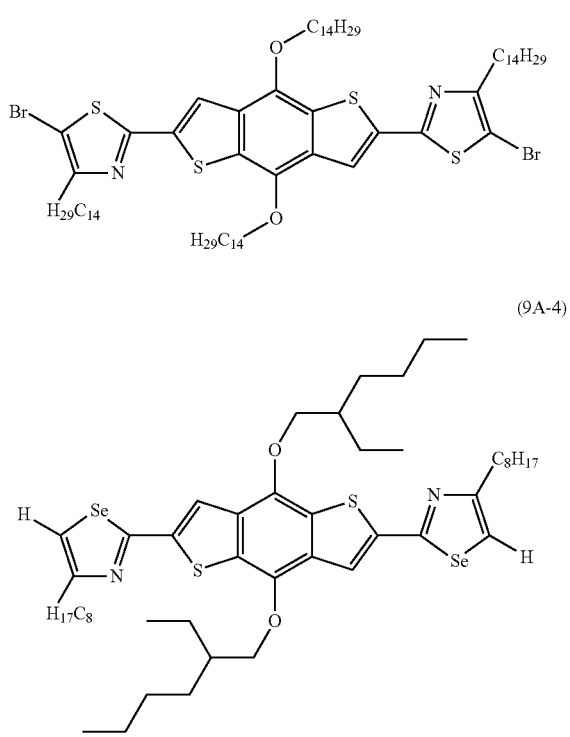

For example, the organic semiconductor compound represented by Chemical Formula 2 may be organic semiconductor compounds including one of structural units represented by the following Chemical Formula 10.

[Chemical Formula 10]
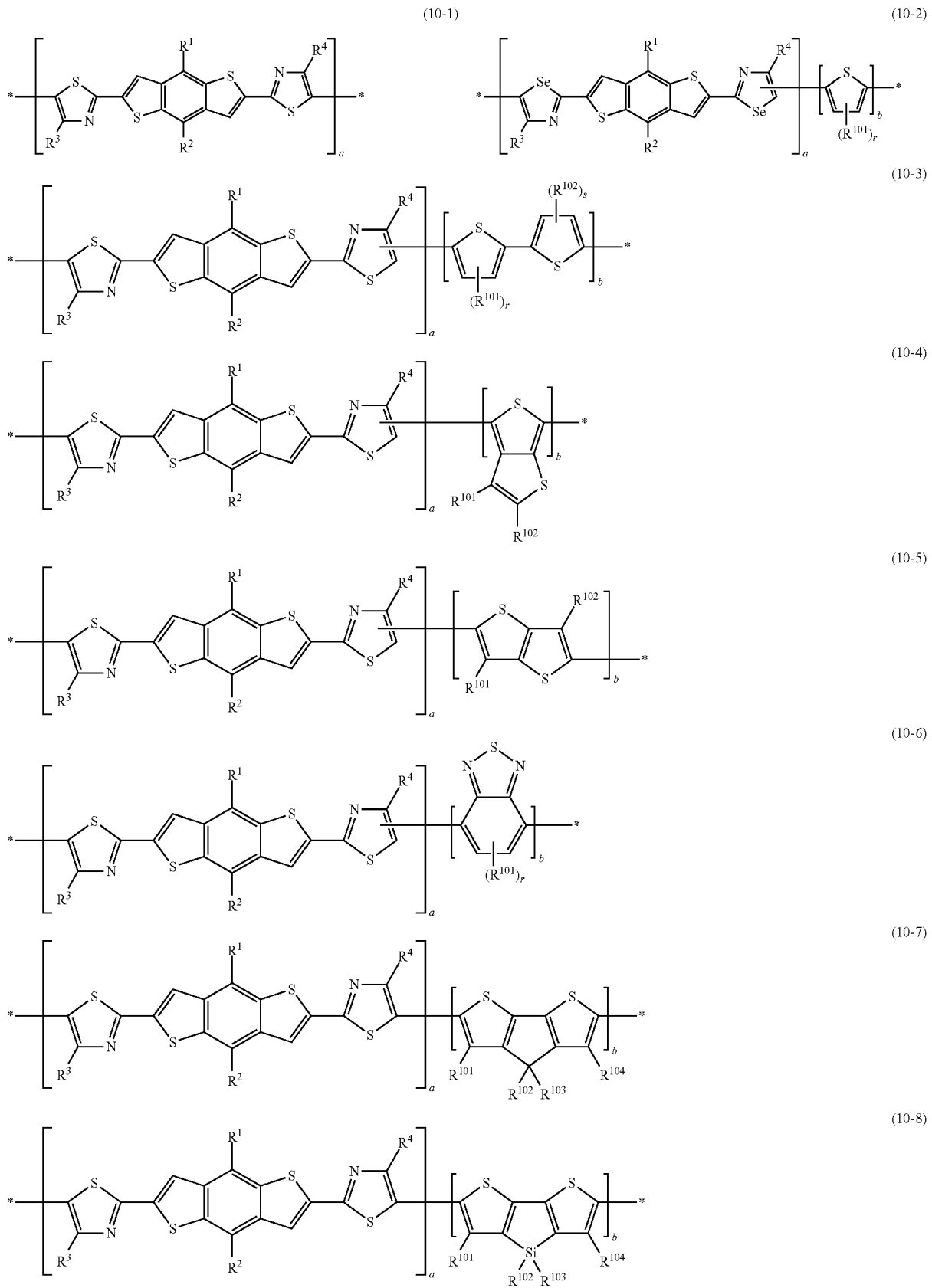

(10-9)
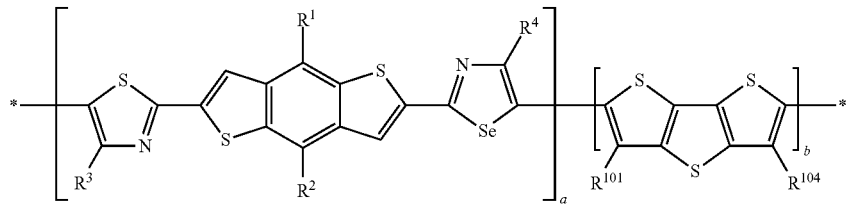
(10-10)
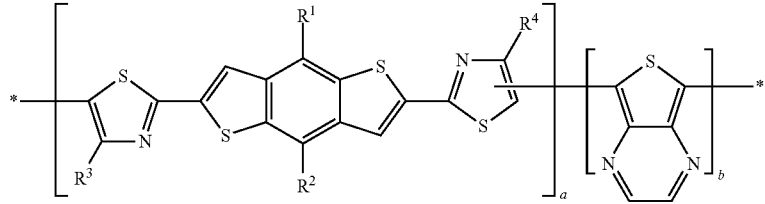
(10-11)
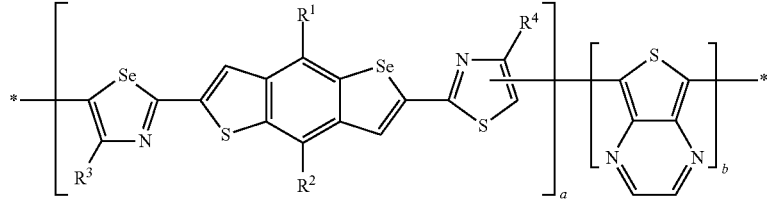
(10-12)
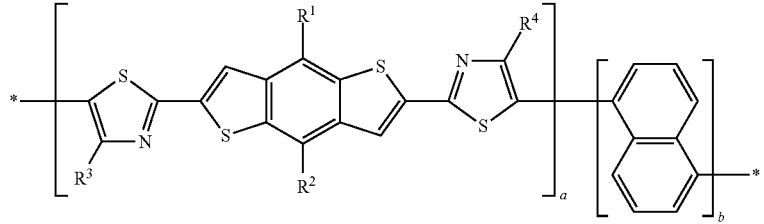
(10-13)
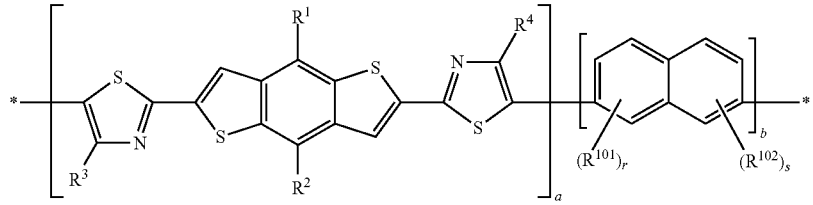
(10-14)
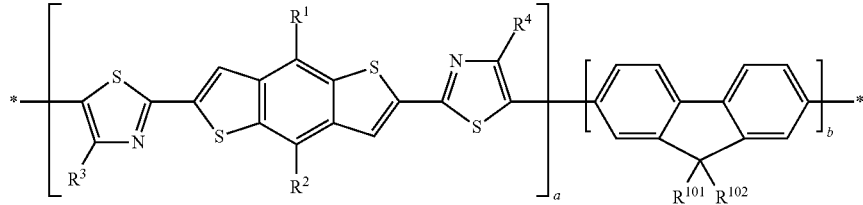
(10-15)
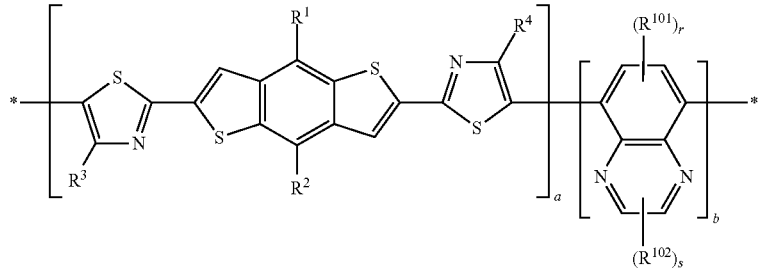

In Chemical Formula 10, $R^1$ to $R^4$ are the same as in Chemical Formula 1, Each of $R^{101}$ and $R^{102}$ are independently selected from hydrogen, a substituted or unsubstituted $C_4$ to $C_{20}$ aromatic ring, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group, r and s are integers of 1 or 2, and a and b represent a mole ratio of each structural unit, wherein a ranges from about 1 mol % to about 100 mol %, and b ranges from about 0 mol % to about 99 mol %, based on a sum, 100 mol % of a and b.

When r and s are 2, a plurality of $R^{101}$ and $R^{102}$ may be the same or different.

For example, the organic semiconductor compound represented by Chemical Formula 2 may be organic semiconductor compounds represented by the following Chemical Formula 10A.

[Chemical Formula 10A]

(10A-1)
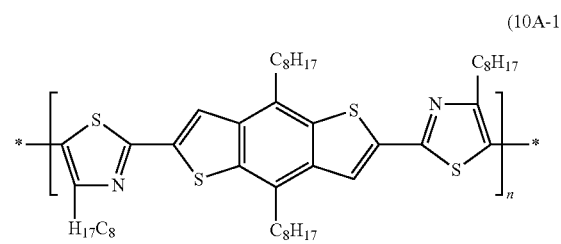

(10A-2)
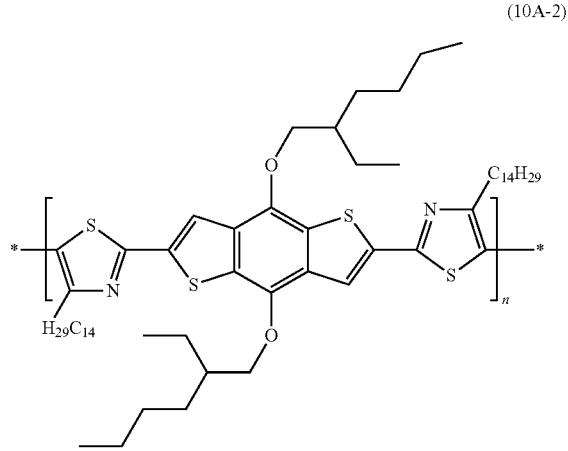

(10A-3)
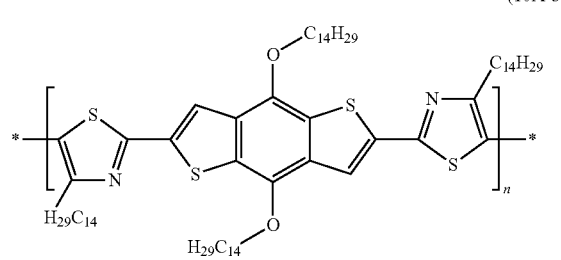

-continued (10A-4)
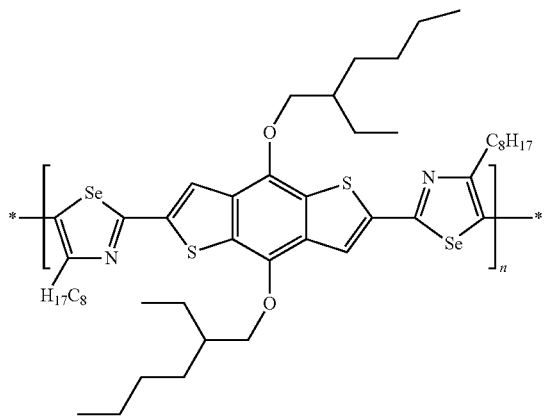

(10A-5)
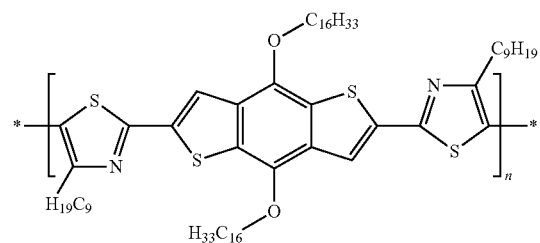

(10A-6)
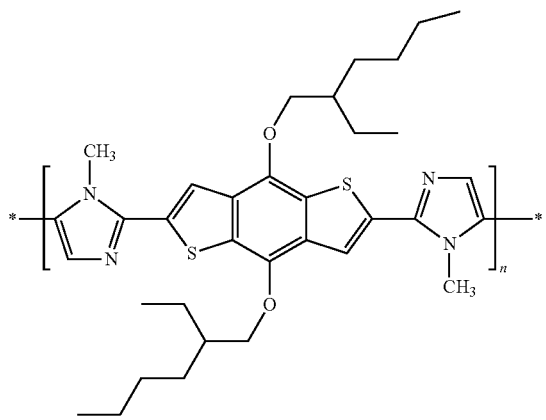

(10A-7)
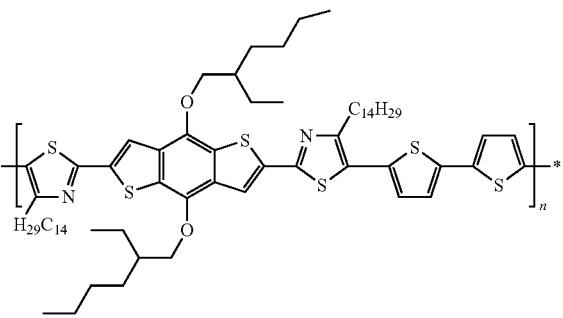

-continued (10A-8)

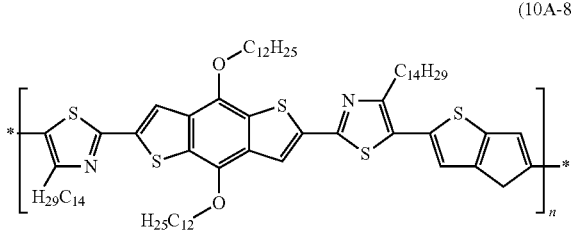

In Chemical Formula 10A, n refers to a degree of polymerization of a polymer, and specifically ranges from 5 to 100.

The organic semiconductor compound represented by Chemical Formula 2 may be an organic semiconductor oligomer or polymer having a number average molecular weight (Mn) of about 5,000 to about 100,000. When the organic semiconductor compound has the number average molecular weight within the range, the dissolubility to the organic solvent may be appropriately controlled to provide a thin film having improved characteristics.

The organic semiconductor compound of the Chemical Formula 1 may be obtained by reacting three monomers of monomer (1), monomer (2), and monomer (3) as shown in the following Reaction Scheme 1.

[Reaction Scheme 1]

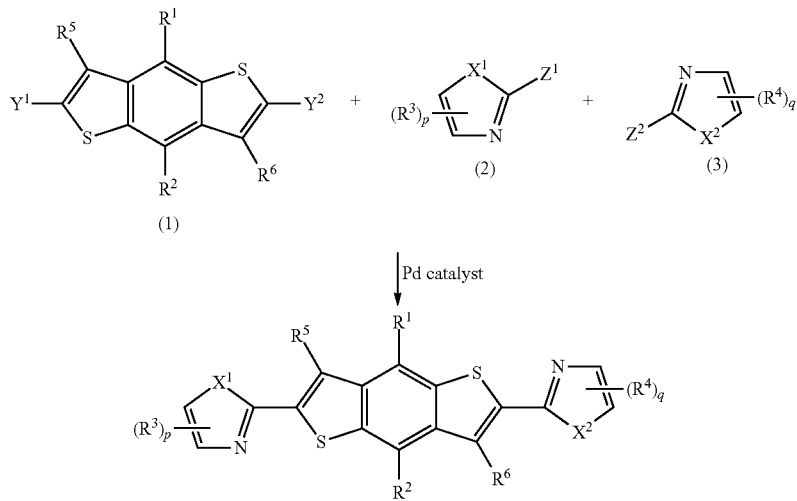

In Reaction Scheme 1, $X^1$, $X^2$, $R^1$ to $R^5$, p, and q are the same as in Chemical Formula 1, each of $Y^1$ and $Y^2$ are independently one of —$Sn(CH_3)_3$, —$Sn(C_4H_9)_3$, and —$B(OR)_2$ (wherein R is hydrogen or a $C_1$ to $C_{10}$ alkyl group), and each of $Z^1$ and $Z^2$ are independently one of —$Sn(CH_3)_3$, —Sn($C_4H_9)_3$, and —$B(OR)_2$ (wherein R is one of hydrogen and a $C_1$ to $C_{10}$ alkyl group), —Br, and —I.

The organic semiconductor compound including the structural unit represented by Chemical Formula 2 may be synthesized as shown in Reaction Scheme 2.

[Reaction Scheme 2]

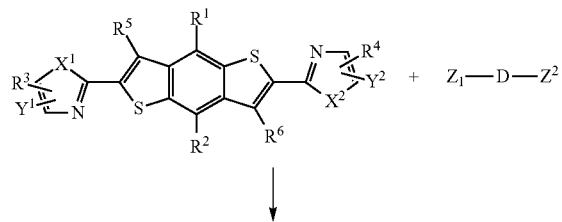

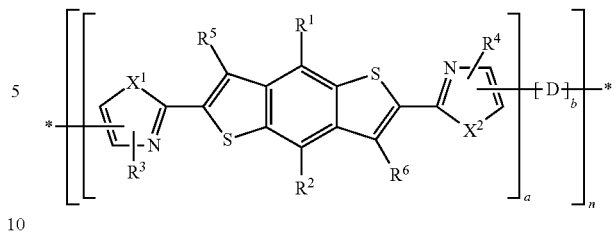

In Reaction Scheme 2, $X^1$, $X^2$ and $R^1$ to $R^5$ are the same as in Chemical Formula 1, -D-, a, and b are the same as in Chemical Formula 2, each of $Y^1$ and $Y^2$ are independently one of —$Sn(CH_3)_3$, —$Sn(C_4H_9)_3$, and —$B(OR)_2$ (wherein R is hydrogen or a $C_1$ to $C_{10}$ alkyl group), each of $Z^1$ and $Z^2$ are independently one of —$Sn(CH_3)_3$, —$Sn(C_4H_9)_3$, —$B(OR)_2$ (wherein R is one of hydrogen and a $C_1$ to $C_{10}$ alkyl group), —Br, and —I, and n represents a degree of polymerization.

According to example embodiments, an organic thin film may include an organic semiconductor compound selected from the organic semiconductor compound represented by Chemical Formula 1, the organic semiconductor compound represented by Chemical Formula 2, and a combination thereof.

The organic thin film according to example embodiments may include the organic semiconductor compound, and may be applied to an organic semiconductor layer for an electronic device, or a carrier transport layer, e.g., a channel layer. The electronic device including the same may have improved electrical properties, e.g., higher charge mobility as well as improved processibility and workability. The organic thin film may be applicable to a transistor, a solar cell, a memory device, an organic light emitting diode (OLED), a photosensor, and/or a laser device.

The organic thin film may be fabricated by depositing the organic semiconductor compound selected from the organic semiconductor compound represented by Chemical Formula 1, the organic semiconductor compound represented by Chemical Formula 2, and a combination thereof on a substrate according to a method, or alternatively dissolving the organic semiconductor compound in an organic solvent and then coating the same on a substrate at room temperature according to a solution process. If required, a heating treatment may be performed after the deposition or coating process to further enhance the densification and uniformity of the thin film. Because the organic semiconductor compound may provide an organic thin film using a solution process, a relatively large-area device may be fabricated at a reduced manufacturing cost of devices.

Particularly, the organic solvent may include at least one kind of organic solvent, for example, at least one kind of an aliphatic hydrocarbon solvent, e.g., one of hexane and heptane, an aromatic hydrocarbon solvent, e.g., one of toluene, pyridine, quinoline, anisole, mesitylene, and xylene, a ketone-based solvent, e.g., one of methyl isobutyl ketone, 1-methyl-2-pyrrolidinone, cyclohexanone, and acetone, an ether-based solvent, e.g., one of tetrahydrofuran and isopropyl ether, an acetate-based solvent, e.g., one of ethyl acetate, butyl acetate, and propylene glycol methyl ether acetate, an alcohol-based solvent, e.g., one of isopropyl alcohol and butanol, an amide-based solvent, e.g., one of dimethyl acetamide and dimethyl formamide, a silicone-based solvent, and a mixture of solvents. The amount of the organic semiconductor compound dissolved in the organic solvent may be adequately selected and determined by a person of ordinary skill in the art, for example, in a range of about 0.01 wt % to about 50 wt % in the total solvent taking into account solubility and coating property.

The method of providing an organic thin film may include thermal deposition, vacuum deposition, laser deposition, screen printing, printing, imprinting, spin casting, dipping, ink jetting, roll coating, flow coating, drop casting, spray coating, and/or roll printing, but is not limited thereto. The heat treatment may be performed at about 80 to about 250° C. for about 1 minute to about 2 hours, but is not limited thereto.

The thickness of the organic thin film may be adjusted according to the usage and the case considering the used compound and solvent by a person of ordinary skill in the art, and may be in a range of about 200 Å to about 10,000 Å.

Hereinafter, example embodiments are illustrated in more detail with reference to examples. However, the following are example embodiments and are not limiting.

Example 1

Synthesis of Organic Semiconductor Compound (7, Monomer)

[Reaction Scheme 3]

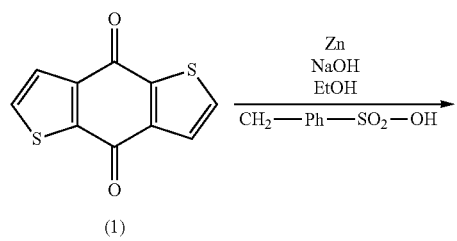

(1)

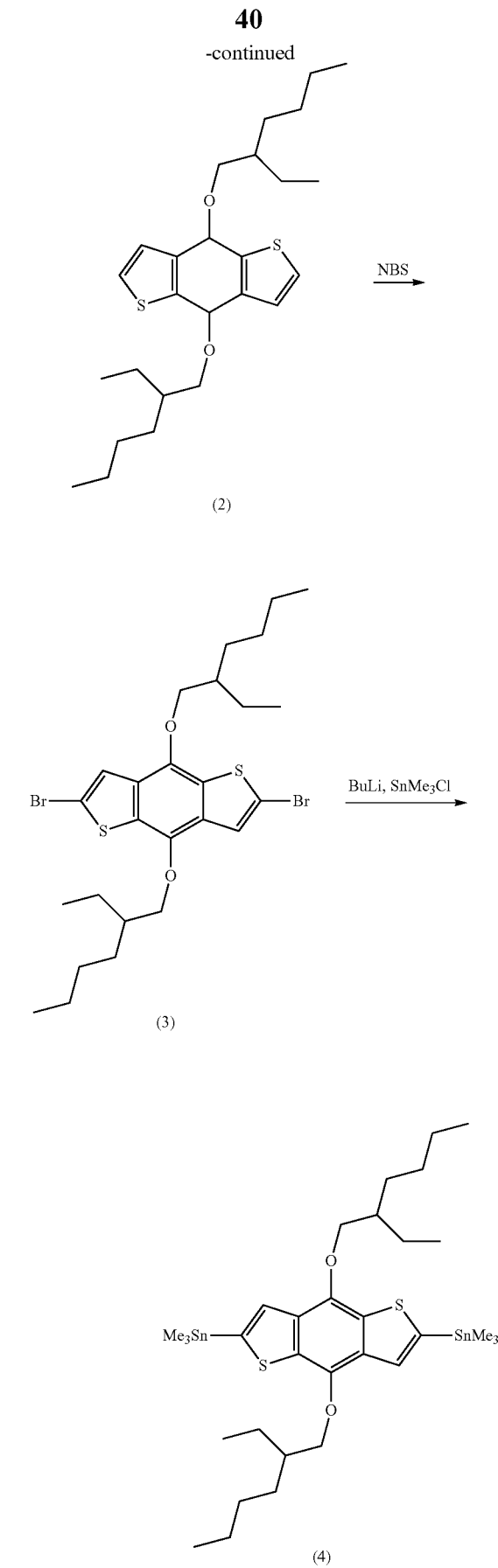

Synthesis Example 1A

Synthesis of compound (2) (4,8-bis(2-ethylhexyloxy)benzo[1,2-b:4,5-b']dithiophene)

NaOH (6 g) is added into a mixture of compound (1) (2.2 g, 10 mmol), Zn powder (1.5 g, 22 mmol), and water (50 ml). The obtained mixture is agitated at 100° C. for 1 hour and added with 1-bromo-2-ethylhexane (30 mmol) and a catalyst amount (1 mol based on 100 mol of monomer) of tetrabutylammonium bromide, and then further reacted for 6 hours. The obtained reaction mixture is introduced into cold water and extracted by diethylether two times to provide an organic layer. The organic layer is dried using MgSO$_4$ and recrystallized in ethanol to provide a colorless crystal of compound (2). The compound (2) has the following $^1$H NMR result.

$^1$H NMR (CDCl$_3$, 300 MHz), δ/ppm: 7.45 (d, 2H), 7.43 (2H, d), 3.92 (4H, m), 1.53 (2H, m), 1.27 (16H, m), 0.88 (12H, m).

Synthesis Example 1B

Synthesis of compound (3) (2,6-dibromo-4,8-di(2-ethylhexyloxy)benzo[1,2-b:4,5-b']dithiophene)

The compound (2) (5.58 g, 10 mmol) is dissolved in 100 mL of methylene chloride and put into ice water. 60 mL of a methylene chloride solution in which bromine (3.2 g, 20 mmol) is dissolved is slowly added thereto in a dropwise fashion. The reaction mixture is reacted for 5 hours until the bromine color disappears in air and recrystallized in hexane to provide a white solid compound (3) (5.5 g).

The compound (3) has the following $^1$H NMR result.

$^1$H NMR (CDCl$_3$, 300 MHz), δ/ppm: 7.48 (2H, s), 3.92 (4H, m), 1.55 (2H, m), 1.27 (12H, m), 0.89 (12H, m).

Synthesis Example 1C

Synthesis of compound (4) (2,6-bis(trimethyltin)-4,8-di(2-ethylhexyloxy)benzo[1,2-b:4,5-b']dithiophene)

The compound (3) (4.3 g, 6 mmol) is dissolved in 100 mL of tetrahydrofuran (THF) under a nitrogen atmosphere and cooled to −70° C. n-butyllithium (13.2 mmol) is slowly added thereto and reacted at −70° C. for about 1 hour. Trimethyltin chloride (14 mmol) is added thereto, and then the temperature is slowly increased. The product is reacted at room temperature of 25° C. for about 2 hours and put in cold water to complete the reaction and extracted with ether two times to provide an organic layer. The obtained organic layer is washed with water. After removing ether under vacuum, the product is recrystallized in ethanol to provide a compound (4) as a colorless needle-shaped crystal (yield of 40%).

The compound (4) has the following $^1$H NMR result.

$^1$H NMR (CDCl$_3$, 300 MHz), δ/ppm: 7.50 (2H, s), 4.19 (4H, m), 1.54 (4H, m), 1.53 (18H, m), 1.10 (12H, m).

Synthesis Example 10

Synthesis of compound (6) (2-trimethyltin-4-tetradecylthiazole)

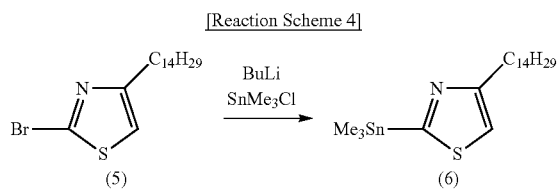

[Reaction Scheme 4]

The compound (5) (2-bromo-4-tetradecylthiazole) (12 g, 34.1 mmol) is dissolved in 100 mL of tetrahydrofuran (THF) under a nitrogen atmosphere and cooled to −75° C. n-butyllithium (24 mL, 38.8 mmol) is slowly added and reacted at −75° C. for about 1 hour. Trimethyltin chloride (Me$_3$SnCl) (9.0 g, 45 mmol) is added thereto, and then the temperature is slowly increased. The product is reacted at room temperature of 25° C. for about 2 hours and put into cold water to complete the reaction and extracted with ether two times to provide an organic layer. The obtained organic layer is washed with water. After removing the ether under vacuum, the product is recrystallized in ethanol to provide a compound (6) (2-trimethyltin-4-tetradecylthiazole as a colorless needle-shaped crystal (6.0 g, 13.6 mmol, yield of 40%).

The compound (6) has the following $^1$H NMR result.

$^1$H NMR (CDCl$_3$, 300 MHz), δ/ppm: 7.03 (1H, s), 2.87 (2H, t), 2.52 (2H, m), 1.23 (22H, m), 0.82 (3H, m), 0.43 (9H, m)

Synthesis Example 1E

Synthesis of Compound (7)

[Reaction Scheme 5]

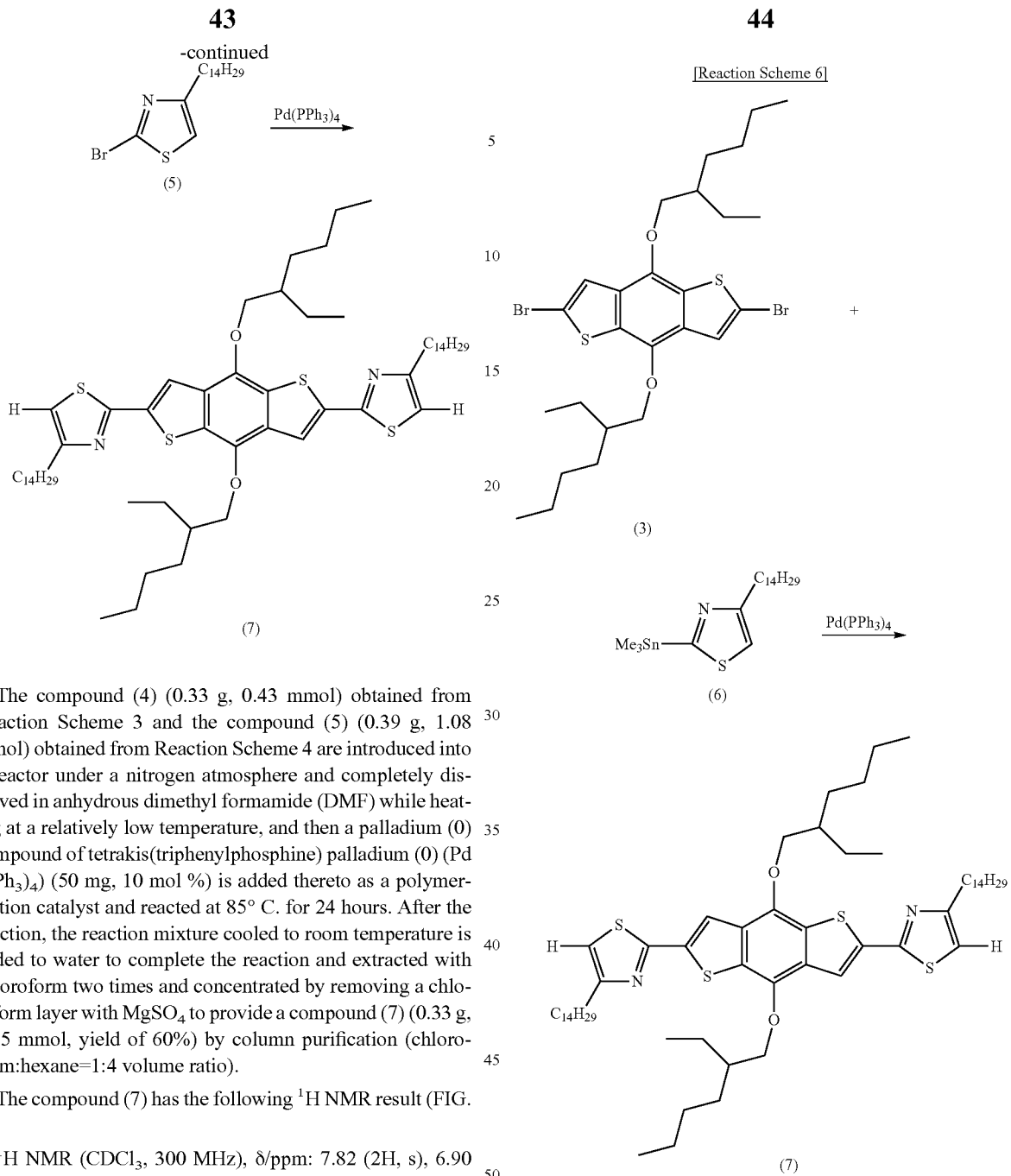

The compound (4) (0.33 g, 0.43 mmol) obtained from Reaction Scheme 3 and the compound (5) (0.39 g, 1.08 mmol) obtained from Reaction Scheme 4 are introduced into a reactor under a nitrogen atmosphere and completely dissolved in anhydrous dimethyl formamide (DMF) while heating at a relatively low temperature, and then a palladium (0) compound of tetrakis(triphenylphosphine) palladium (0) (Pd(PPh$_3$)$_4$) (50 mg, 10 mol %) is added thereto as a polymerization catalyst and reacted at 85° C. for 24 hours. After the reaction, the reaction mixture cooled to room temperature is added to water to complete the reaction and extracted with chloroform two times and concentrated by removing a chloroform layer with MgSO$_4$ to provide a compound (7) (0.33 g, 0.25 mmol, yield of 60%) by column purification (chloroform:hexane=1:4 volume ratio).

The compound (7) has the following $^1$H NMR result (FIG. 1).

$^1$H NMR (CDCl$_3$, 300 MHz), δ/ppm: 7.82 (2H, s), 6.90 (2H, s), 4.23 (4H, d), 1.84-1.51 (12H, m), 1.45-1.25 (52H, broad), 1.05-0.87 (18H, m)

Synthesis Example 1F

Synthesis of Compound (7)

As shown in the following Reaction Scheme 6, the compound (3) obtained from Reaction Scheme 3 and the compound (6) obtained from the Reaction Scheme 4 are reacted to provide an organic semiconductor compound (7).

$^1$H NMR (CDCl$_3$, 300 MHz), δ/ppm: 7.82 (2H, s), 6.90 (2H, s), 4.23 (4H, d), 1.84-1.51 (12H, m), 1.45-1.25 (52H, broad), 1.05-0.87 (18H, m).

Example 2

Synthesis of Organic Semiconductor Compound (7-1) (Monomer)

Figure 2:
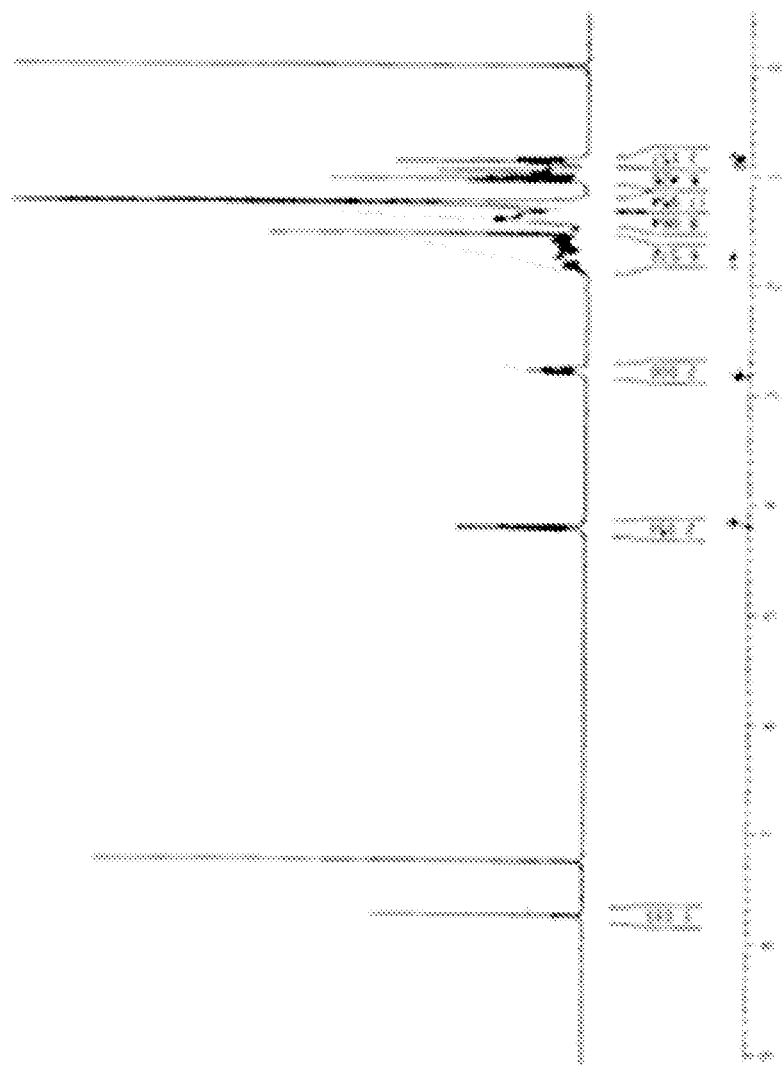

The compound (7) obtained from Example 1 is reacted with NBS (N-bromosuccinimide) in a chloroform solvent to provide compound (7-1) (yield=76%). The compound (7-1) has the following $^1$H NMR result (FIG. 2).

$^1$H NMR (CDCl$_3$, 300 MHz), δ/ppm: 7.74 (2H, s), 4.22 (4H, d), 1.84-1.52 (12H, m), 1.06-1.25 (52H, broad), 1.05-0.85 (18H, m)

[Reaction Scheme 7]

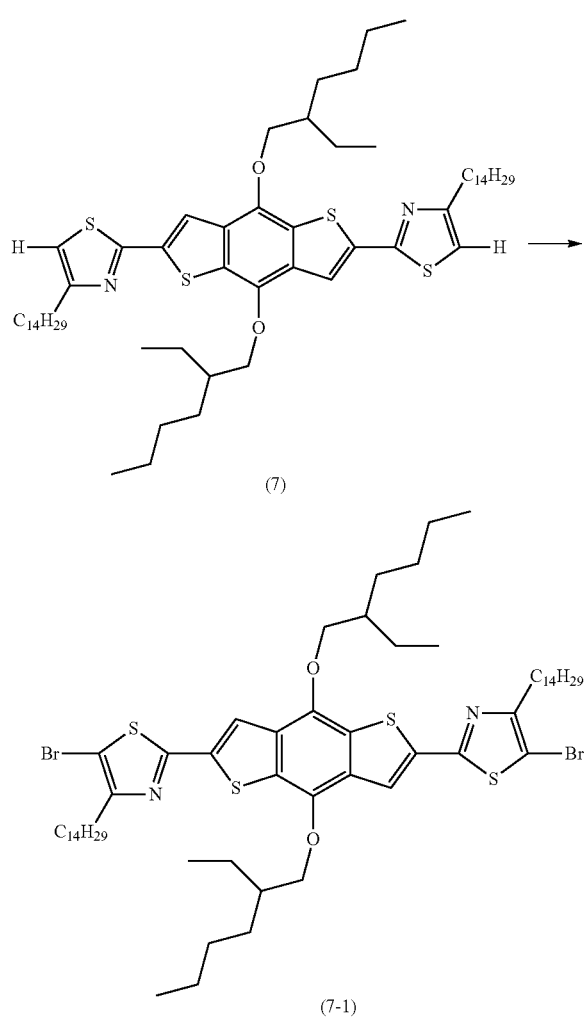

Example 3

Synthesis of Organic Semiconductor Compound (8) (Monomer)

[Reaction Scheme 8]

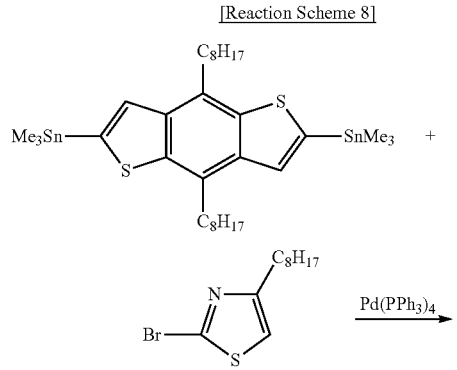

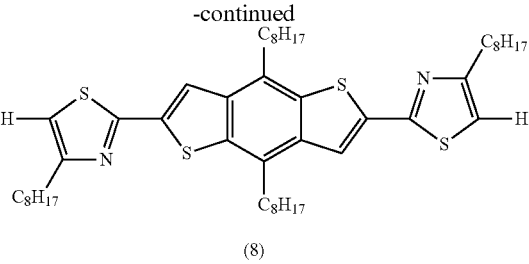

2,6-bis(trimethyltin)-4,8-di(2-octyl)benzo[1,2-b:4,5-b'] dithiophene (1.08 g, 1.5 mmol) and 2-bromo-4-octylthiazole (1.0 g, 3.6 mmol) are completely dissolved in anhydrous dimethyl formamide (DMF) while heating at a relatively low temperature in a reactor under the nitrogen atmosphere, and then a palladium (0) compound of tetrakis(triphenylphosphine) palladium (0) (Pd(PPh$_3$)$_4$) (0.17 g, 1.5 mol %) is added thereto as a polymerization catalyst and reacted at 90° C. for 48 hours. After the reaction, the reaction mixture cooled to room temperature (25° C.) is added to water to complete the reaction and extracted with chloroform two times and concentrated by removing a chloroform layer with MgSO$_4$ to provide compound (8) (0.69 g, 0.84 mmol, yield 56%) by column purification (chloroform:hexane=1:4 volume ratio).

$^1$H NMR (CDCl$_3$, 300 MHz), δ/ppm: 7.82 (2H, s), 6.89 (2H, s), 3.20 (4H, t), 2.87 (4H, t), 1.84-1.51 (16H, m), 1.45-1.25 (32H, broad), 1.05-0.87 (12H, m).

Example 4

Synthesis of Organic Semiconductor Compound (9) (Monomer)

[Reaction Scheme 9]

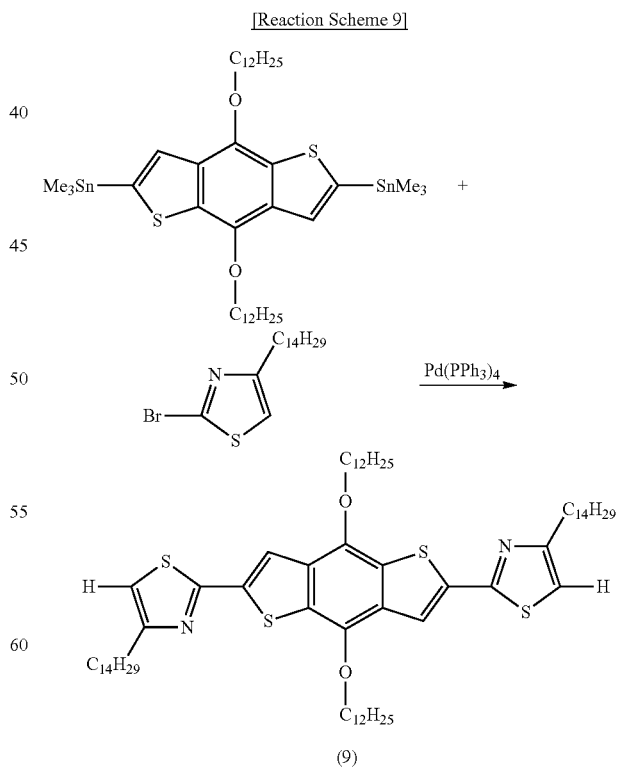

2,6-bis(trimethyltin)-4,8-di(2-decyloxy)benzo[1,2-b:4,5-b']dithiophene (1.77 g, 2.0 mmol) and 2-trimethyltin-4-tetradecylthiazole (0.9 g, 2.5 mmol) are completely dissolved in anhydrous dimethyl formamide (DMF) while heating at a relatively low temperature in a reactor under a nitrogen atmosphere, and then a palladium (0) compound of tetrakis(triphenylphosphine) palladium (0) (Pd(PPh$_3$)$_4$) (0.23 g, 0.2 mol %) is added thereto as a polymerization catalyst and reacted at 95° C. for 48 hours. After the reaction, the reaction mixture cooled to room temperature (25° C.) is added to water to complete the reaction and extracted with chloroform two times and concentrated by drying the chloroform layer with MgSO$_4$ to provide compound (9) (1.1 g, 1.03 mmol, yield of 52%) by column purification (chloroform:hexane=1:4 volume ratio).

$^1$H NMR (CDCl$_3$, 300 MHz), δ/ppm: 7.82 (2H, s), 6.90 (2H, s), 4.23 (4H, t), 1.54 (16H, m), 1.45-1.25 (76H, broad), 0.89 (12H, m).

Example 5

Synthesis of Organic Semiconductor Compound (10) (Polymer)

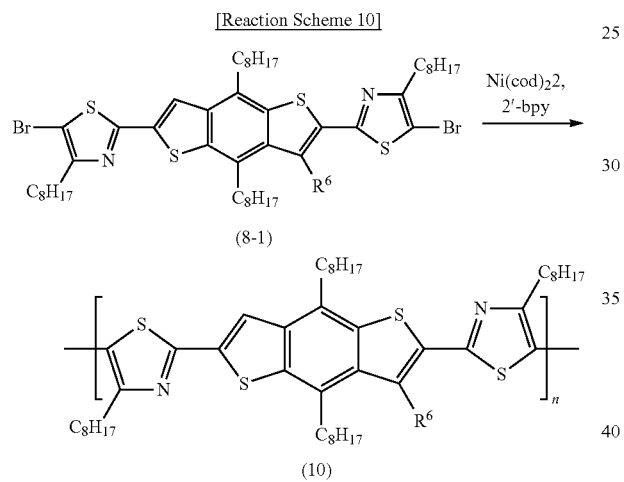

In Reaction Scheme 10, n refers to a degree of polymerization and is determined according to a molecular weight.

The compound (8) according to Example 3 is reacted with NBS (N-bromosuccinimide) in a chloroform solvent in accordance with the same procedure as in Example 2 to provide a compound (8-1). In a reactor under a nitrogen atmosphere, a nickel (0) compound (Ni(cod)$_2$, 0.5 g, 1.9 mmol), bipyridine (bpy, 0.3 g, 1.9 mmol), and cyclooctadiene (0.22 g) are added into anhydrous DMF (10 mL) and agitated at 60° C. for 30 minutes, and then the compound (8-1) (1.6 g, 1.3 mmol) is added thereto and agitated at about 80° C. for about 48 hours. After the reaction, the reaction solution cooled to room temperature of 25° C. is added to about 1.2 L of a mixed solution of ammonia water/methanol (1:2 volume ratio) and agitated for about 12 hours to complete the reaction, and then filtered under reduced pressure. The obtained reactant is dissolved in chloroform and washed with a hydrochloric acid aqueous solution, ammonia water, and water each for 12 hours to provide a chloroform solution. The obtained chloroform solution is concentrated and reprecipitated in methanol and dried for 24 hours to provide an organic semiconductor compound (10) (yield=75%, number average molecular weight=about 15,000 (measured by GPC (gel permeation chromatography)).

The organic semiconductor compound (10) has the following $^1$H NMR result.

$^1$H NMR (CDCl$_3$, 300 MHz), δ/ppm: 7.08, 4.24, 2.95, 1.85-1.6, 1.59-1.2, 1.19-0.85.

Example 6

Synthesis of Organic Semiconductor Compound (11) (Polymer)

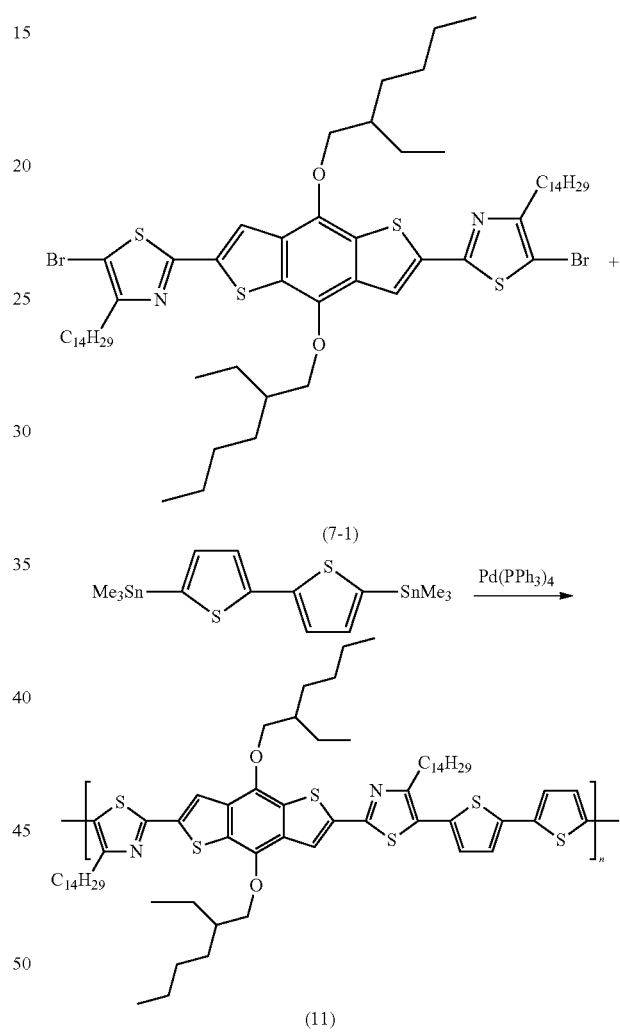

In Reaction Scheme 11, n refers to a degree of polymerization and is determined according to a molecular weight.

The compound (7-1) (0.5 g, 0.38 mmol) according to Example 2 and bis(trimethylstannyl)bithiophene (0.19 g, 0.38 mmol) are introduced into a reactor under a nitrogen atmosphere and completely dissolved in anhydrous DMF while heating at a relatively low temperature, and then a palladium (0) compound of tetrakis(triphenylphosphine) palladium (0) (Pd(PPh$_3$)$_4$) (44 mg, 10 mol %) is added thereto as a polymerization catalyst and reacted at 85° C. for 5 hours. 2-tributylstannyl thiophene is added in excess amount (1.4 g, 3.8 mmol) based on the compound (7-1) and reacted for 24 hours. After the reaction, the reaction mixture cooled to room temperature of 25° C. is filtered to provide a polymer solid. The polymer solid is washed with a hydrochloric acid aqueous solution/chloroform two times, an ammonia aqueous solution/chloroform two times, and water/chloroform two times, and then the polymer is recovered by Soxhlet extraction using methanol, acetone, methylene chloride, and chloroform. After drying, the organic semiconductor compound (11) is obtained (yield=46%, number average molecular weight=about 20,000, measured by GPC (gel permeation chromatography).

The organic semiconductor compound (11) has the following $^1$H NMR result.

$^1$H NMR (CDCl$_3$, 300 MHz), δ/ppm: 7.08, 6.60, 4.24, 2.95, 1.85-1.6, 1.59-1.2, 1.19-0.85, Example 7

Synthesis of Organic Semiconductor Compound (12) (Polymer)

[Reaction Scheme 12]

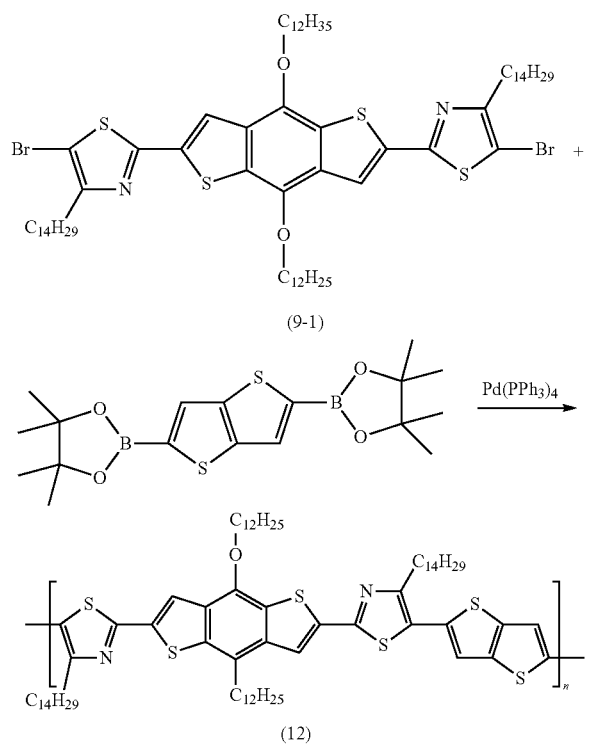

In Reaction Scheme 12, n refers to a degree of polymerization and is determined according to a molecular weight.

The compound (9-1) (0.4 g, 0.32 mmol) and 2,6-bis(boronic acid pinacol ester)thieno[3,2-b]thiophene (0.12 g, 0.32 mmol) are introduced into a reactor under a nitrogen atmosphere and completely dissolved in toluene while heating at a relatively low temperature, and then added with 5 ml of a solution in which a palladium (0) compound of tetrakis(triphenylphosphine) palladium (0) (Pd(PPh$_3$)$_4$) (36 mg, 10 mol %) and Aliquat™ 336 (Starks' catalyst) (60 mg) are dissolved in toluene as a polymerization catalyst, and 2 M of a Na$_2$CO$_3$ aqueous solution (4 mL), and reacted at 90° C. for 24 hours. After the reaction, the reaction mixture cooled to room temperature of 25° C. is filtered to provide a polymer solid. The polymer solid is washed with a hydrochloric acid aqueous solution/chloroform two times, an ammonia aqueous solution/chloroform two times, and water/chloroform two times, and then the polymer is recovered by Soxhlet extraction using methanol, acetone, methylene chloride, and chloroform. After drying, the organic semiconductor compound (12) is obtained (yield=46%, number average molecular weight=about 20,000, measured by GPC (gel permeation chromatography).

The organic semiconductor compound (12) has the following $^1$H NMR result.

$^1$H NMR (CDCl$_3$, 300 MHz), δ/ppm: 7.16 2H, 6.88 2H, 4.23 4H, 1.54 8H, 1.45-1.25 36H, 0.89 6H.

Figure 3:
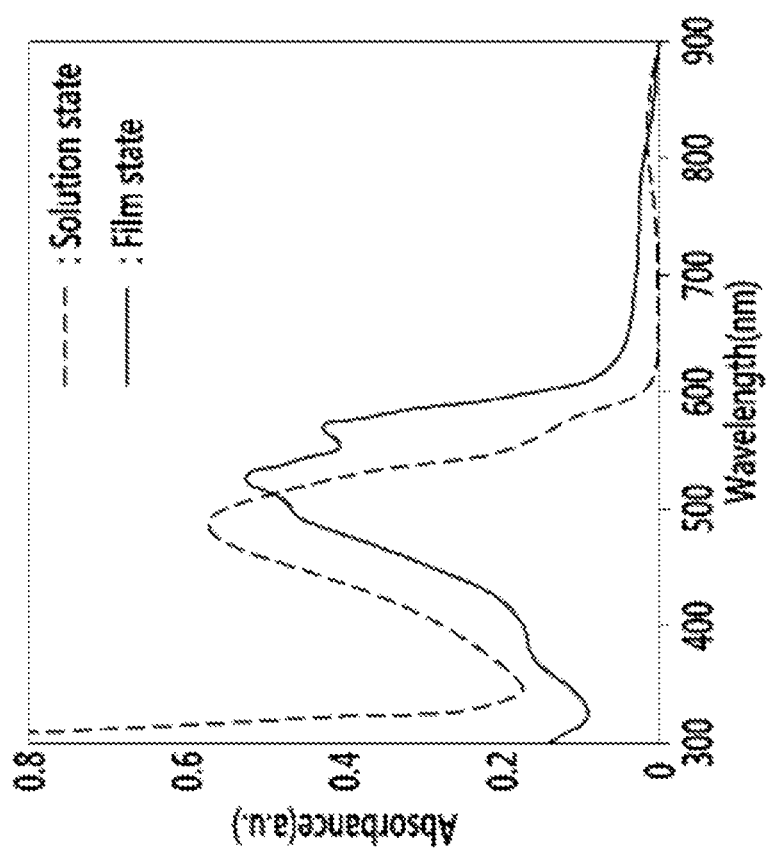

The organic semiconductor compound (11) obtained from Example 6 is dissolved in a chloroform solvent at a concentration of 1.0 wt % and coated by spin-coating and baked at 100° C. for 1 hour under a nitrogen atmosphere to provide a film. FIG. 3 shows UV absorption spectra of the organic semiconductor compound (11) according to Example 6 in a solution state dissolved in a chloroform solvent and a film state. As shown in FIG. 3, the organic semiconductor compound (11) according to Example 6 is confirmed to shift into the longer wavelength in the film state. In the film state, the arrangement and stacking between molecules are well achieved.

FIG. 4 shows a differential scanning calorimetry (DSC) analysis result of the organic semiconductor compound (11) according to Example 6. As is clear from FIG. 4, the organic semiconductor compound (11) has improved thermal stability.

While this disclosure has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:
1. An organic semiconductor compound comprising a structural unit represented by the following Chemical Formula 2:

[Chemical Formula 2]

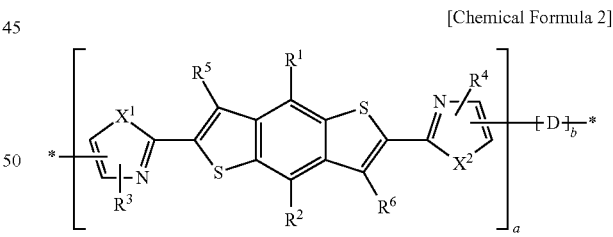

wherein, in Chemical Formula 2
each of X$^1$ and X$^2$ are independently one of S, Se, and NR$^a$ (wherein, R$^a$ is hydrogen, a substituted or unsubstituted C$_1$ to C$_{30}$ linear or branched alkyl group, a substituted or unsubstituted C$_3$ to C$_{20}$ cycloalkyl group, a substituted or unsubstituted C$_1$ to C$_{30}$ linear or branched alkoxy group, a substituted or unsubstituted C$_6$ to C$_{30}$ aryl group, a substituted or unsubstituted C$_7$ to C$_{30}$ arylalkyl group, and a substituted or unsubstituted C$_2$ to C$_{30}$ heteroaryl group),
each of R$^1$ and R$^2$ are independently selected from a halogen (—F, —Cl, —Br, or —I), a substituted or unsubstituted C$_1$ to C$_{30}$ linear or branched alkyl group, a substituted or unsubstituted C$_3$ to C$_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, a substituted or unsubstituted $C_2$ to $C_{30}$ heteroaryl group, —$COR^b$ (wherein $R^b$ is selected from a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group), and —$C(=O)OR^c$ (wherein $R^c$ is selected from hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group), each of $R^3$ and $R^4$ are a combination of A and B, wherein each A is a halogen (—F, —Cl, —Br, or —I), and each B is independently selected from a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, a substituted or unsubstituted $C_2$ to $C_{30}$ heteroaryl group, —$COR^b$ (wherein $R^b$ is selected from a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group), and —$C(=O)OR^c$ (wherein $R^c$ is selected from hydrogen, a substituted or unsubstituted $C_1$ to $C_{30}$ linear or branched alkyl group, a substituted or unsubstituted $C_3$ to $C_{20}$ cycloalkyl group a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group), each of $R^5$ and $R^6$ are independently one of hydrogen and a $C_1$ to $C_{10}$ alkyl group, -D- is one of a substituted or unsubstituted $C_4$ to $C_{20}$ aromatic ring, a substituted or unsubstituted $C_4$ to $C_{14}$ heteroaromatic ring, and a substituted or unsubstituted $C_6$ to $C_{30}$ condensed polycyclic group including a heteroaromatic ring, and a and b represent a mole ratio of each structural unit, wherein a is greater than or equal to about 1 mol % and is less than about 100 mol %, and b is greater than 0 mol % and is less than or equal to about 99 mol %, based on a sum, 100 mol % of a and b.

2. The organic semiconductor compound of claim 1, wherein the -D- structural unit is one of the structural units represented by the following Chemical Formula 3:

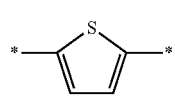
(1)

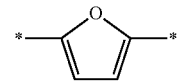
(2)

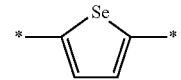
(3)

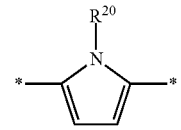
(4)

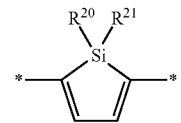
(5)

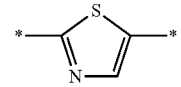
(6)

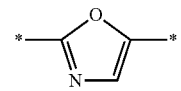
(7)

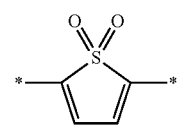
(8)

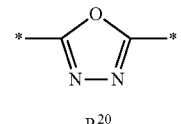
(9)

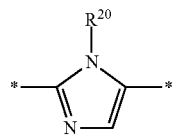
(10)

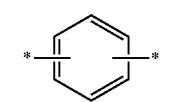
(11)

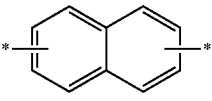
(12)

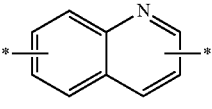
(13)

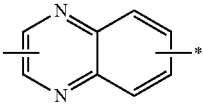
(14)

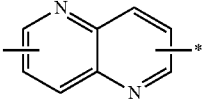
(15)

-continued
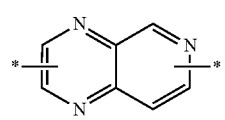 (16)
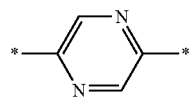 (17)
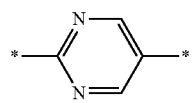 (18)
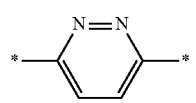 (19)
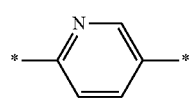 (20)
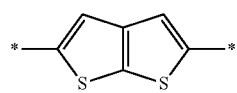 (21)
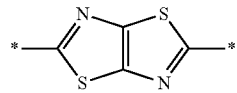 (22)
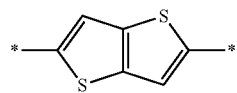 (23)
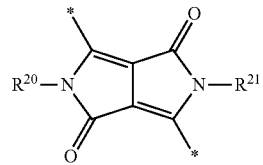 (24)
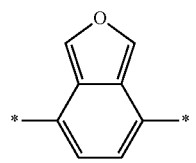 (25)
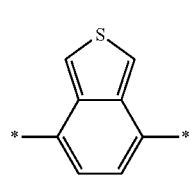 (26)
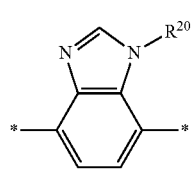 (27)
-continued
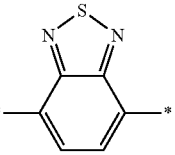 (28)
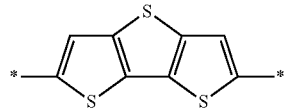 (29)
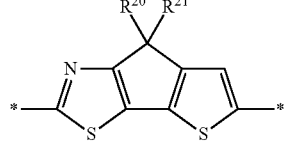 (30)
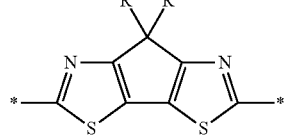 (31)
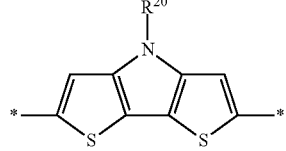 (32)
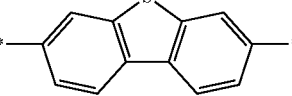 (33)
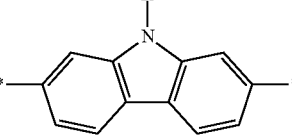 (34)
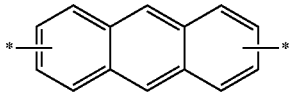 (35)
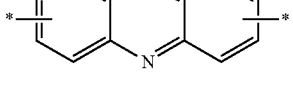 (36)
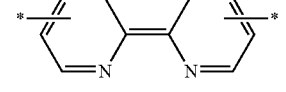 (37)
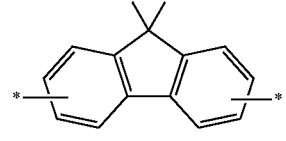 (38)

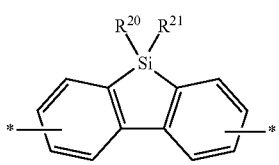
(39)
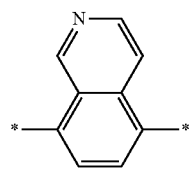
(40)
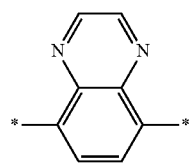
(41)
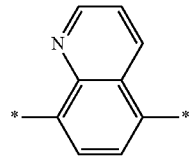
(42)
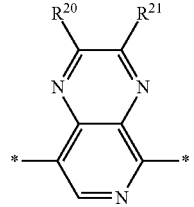
(43)
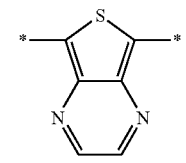
(44)
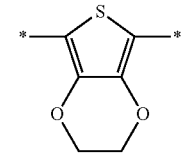
(45)
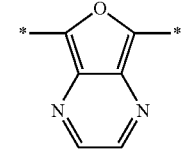
(46)
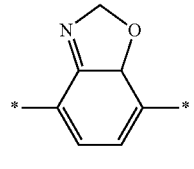
(47)
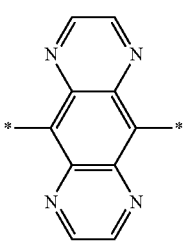
(48)
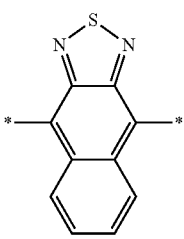
(49)
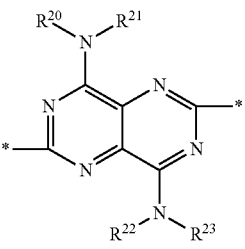
(50)
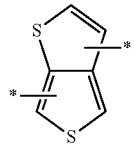
(51)
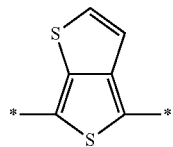
(52)
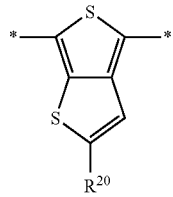
(53)
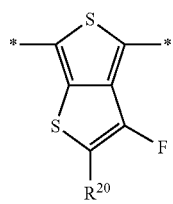
(54)
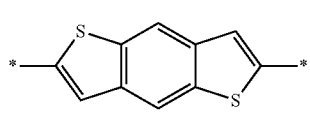
(55)

-continued

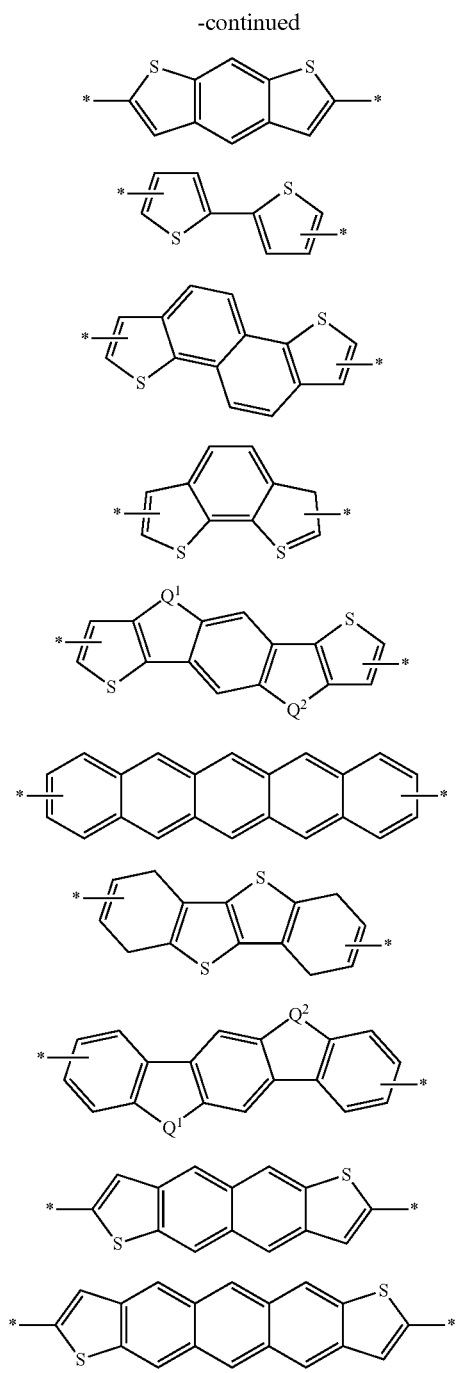

wherein in Chemical Formula 3,
each of $R^{20}$ to $R^{23}$ are independently selected from hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, a substituted or unsubstituted $C_2$ to $C_{30}$ heteroaryl group, and a combination thereof,
each of $Q^1$ and $Q^2$ are independently one of S, $CR^{24}R^{25}$, $NR^{26}$ and $SiR^{27}R^{28}$, wherein each of $R^{24}$ to $R^{28}$ are independently selected from hydrogen, a substituted or unsubstituted $C_1$ to $C_{15}$ linear or branched alkyl group, a substituted or unsubstituted $C_3$ to $C_{15}$ cycloalkyl group, a substituted or unsubstituted $C_1$ to $C_{15}$ alkoxy group, a substituted or unsubstituted $C_6$ to $C_{15}$ aryl group, a substituted or unsubstituted $C_2$ to $C_{15}$ heteroaryl group, and a combination thereof, and
hydrogen of —CH— or —CH$_2$— positioned in the aromatic ring or heteroaromatic ring of the above Chemical Formula 3 is optionally substituted with one selected from a fluoro group, a $C_1$ to $C_{10}$ fluoroalkyl group, a $C_1$ to $C_{20}$ linear or branched alkyl group, a $C_3$ to $C_{20}$ cycloalkyl group, a $C_1$ to $C_{20}$ alkoxy group, a substituted or unsubstituted $C_6$ to $C_{30}$ aryl group, and a substituted or unsubstituted $C_2$ to $C_{30}$ heteroaryl group.

3. The organic semiconductor compound of claim 1, wherein the -D- structural unit is a structural unit represented by the following Chemical Formula 4 including a substituted or unsubstituted thiophene structural unit:

[Chemical Formula 4]

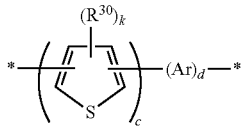

wherein, in Chemical Formula 4,
$R^{30}$ is selected from hydrogen, a substituted or unsubstituted $C_4$ to $C_{20}$ aromatic ring, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group,
k is an integer of 1 or 2,
-Ar- is one of a substituted or unsubstituted $C_4$ to $C_{20}$ aromatic ring, a substituted or unsubstituted $C_4$ to $C_{14}$ heteroaromatic ring, and a substituted or unsubstituted $C_6$ to $C_{30}$ condensed polycyclic group including a heteroaromatic ring, and
c and d represent a mole ratio of each structural unit, wherein c ranges from about 1 mol % to about 99 mol %, and d ranges from 1 to from 99 mol % based on a sum, 100 mol % of c and d.

4. The organic semiconductor compound of claim 3, wherein -Ar- of the Chemical Formula 4 is one of the above structural units represented by Chemical Formula 3:

[Chemical Formula 3]

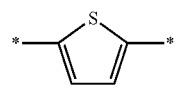 (1)

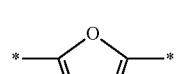 (2)

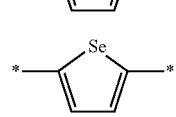 (3)

-continued
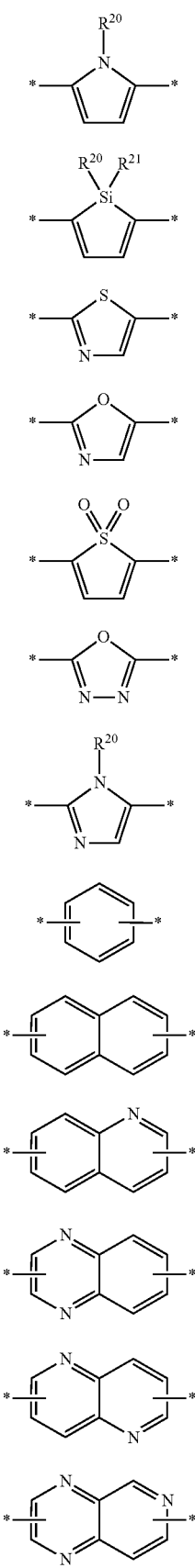
(4)
(5)
(6)
(7)
(8)
(9)
(10)
(11)
(12)
(13)
(14)
(15)
(16)
-continued
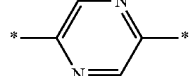 (17)
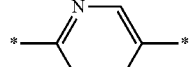 (18)
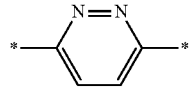 (19)
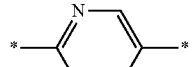 (20)
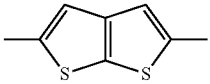 (21)
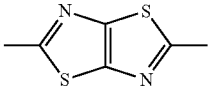 (22)
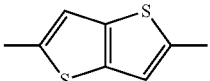 (23)
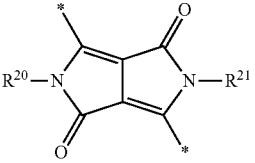 (24)
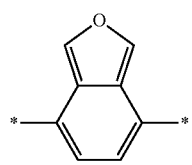 (25)
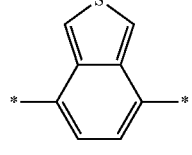 (26)
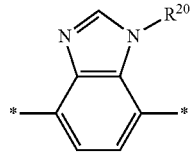 (27)
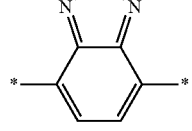 (28)

-continued

(49) 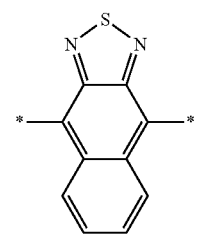

(50) 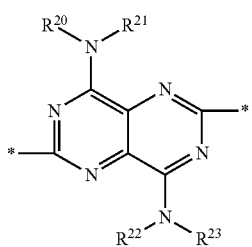

(51) 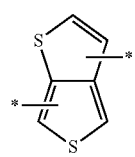

(52) 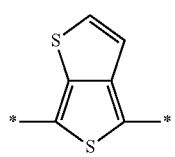

(53) 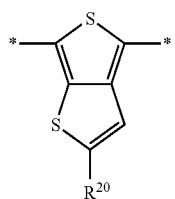

(54) 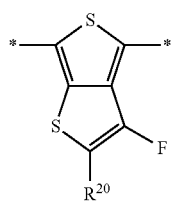

(55) 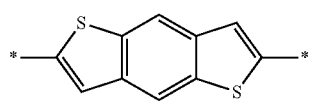

(56) 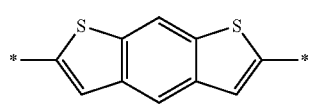

(57) 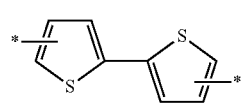

(58) 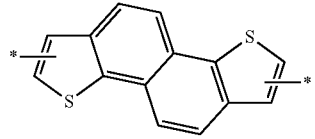

(59) 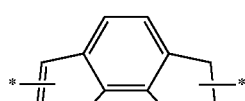

(60) 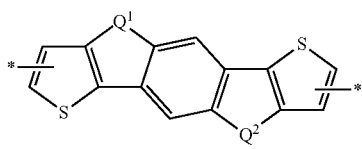

(61) 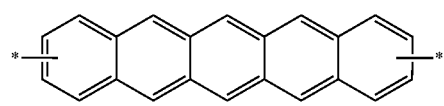

(62) 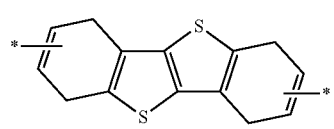

(63) 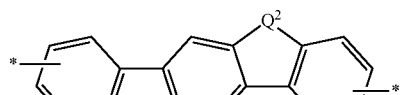

(64) 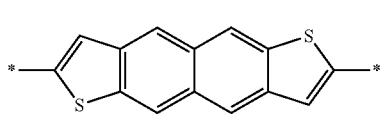

(65) 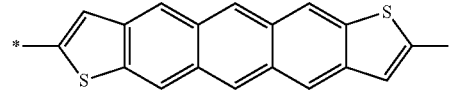

wherein, in Chemical Formula 3, each of $R^{20}$ to $R^{23}$ are independently selected from hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, a substituted or unsubstituted $C_2$ to $C_{30}$ heteroaryl group, and a combination thereof, each of $Q^1$ and $Q^2$ are independently one of S, $CR^{24}R^{25}$, $NR^{26}$ and $SiR^{27}R^{28}$, wherein each of $R^{24}$ to $R^{28}$ are independently selected from hydrogen, a substituted or unsubstituted $C_1$ to $C_{15}$ linear or branched alkyl group, a substituted or unsubstituted $C_3$ to $C_{15}$ cycloalkyl group, a substituted or unsubstituted $C_1$ to $C_{15}$ alkoxy group, a substituted or unsubstituted $C_6$ to $C_{15}$ aryl group, a substituted or unsubstituted $C_2$ to $C_{15}$ heteroaryl group, and a combination thereof, and a hydrogen of —CH— or —CH$_2$— positioned in the aromatic ring or heteroaromatic ring of the above Chemical Formula 3 is optionally substituted with one selected from a fluoro group, a $C_1$ to $C_{10}$ fluoroalkyl group, a $C_1$ to $C_{20}$ linear or branched alkyl group, a $C_3$ to $C_{20}$ cycloalkyl group, a $C_1$ to $C_{20}$ alkoxy group, a substituted or unsubstituted $C_6$ to $C_{30}$ aryl group, and a substituted or unsubstituted $C_2$ to $C_{30}$ heteroaryl group.

5. The organic semiconductor compound of claim 1, wherein the organic semiconductor compound represented by Chemical Formula 2 includes one of terminal functional groups represented by the following Chemical Formulas 5 to 8:

[Chemical Formula 5]

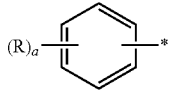

wherein, in the above Chemical Formula 5,
R is one of a fluoro group and a $C_1$ to $C_{20}$ perfluoroalkyl group, and a is an integer ranging from 1 to 5,

[Chemical Formula 6]

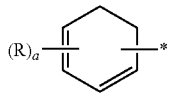

wherein, in the above Chemical Formula 6,
R is one of a fluoro group and a $C_1$ to $C_{20}$ perfluoroalkyl group, and a is an integer ranging from 1 to 6, and

[Chemical Formula 7]

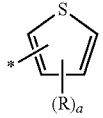

wherein, in the above Chemical Formula 7,
R is one of a fluoro group and a $C_1$ to $C_{20}$ perfluoroalkyl group, and a is an integer ranging from 1 to 3, and

[Chemical Formula 8]

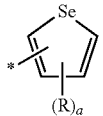

wherein, in the above Chemical Formula 8,
R is one of a fluoro group and a $C_1$ to $C_{20}$ perfluoroalkyl group, and a is an integer ranging from 1 to 3.

6. The organic semiconductor compound of claim 1, wherein the organic semiconductor compound represented by Chemical Formula 2 includes one of structural units represented by the following Chemical Formula 10:

[Chemical Formula 10]

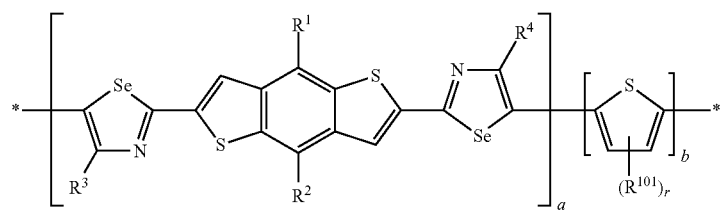

(10-2)

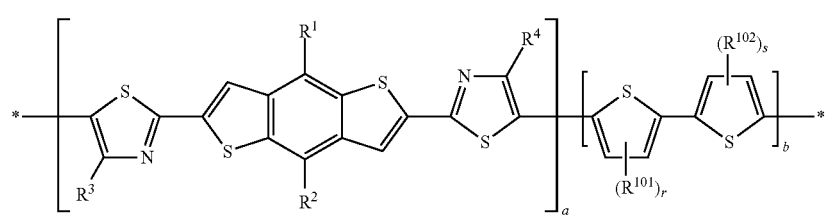

(10-3)

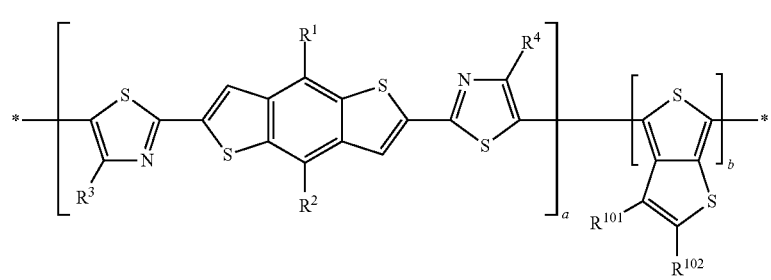

(10-4)

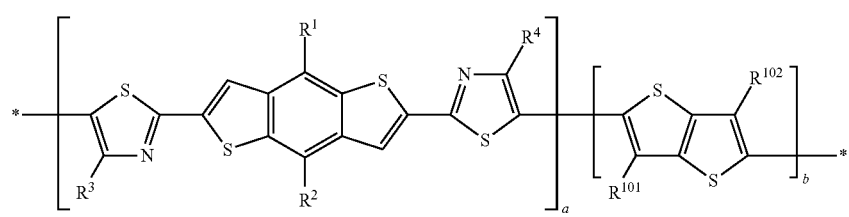

(10-5)

-continued
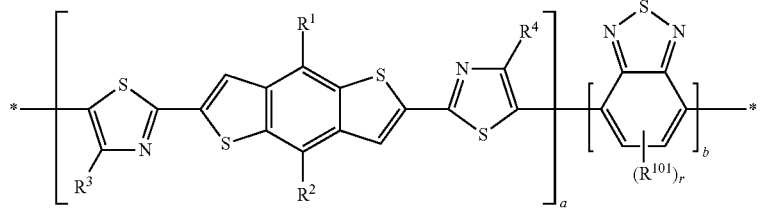 (10-6)
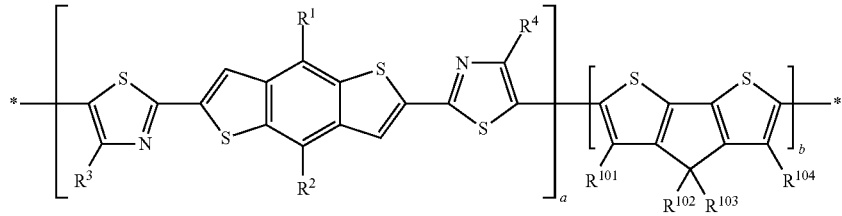 (10-7)
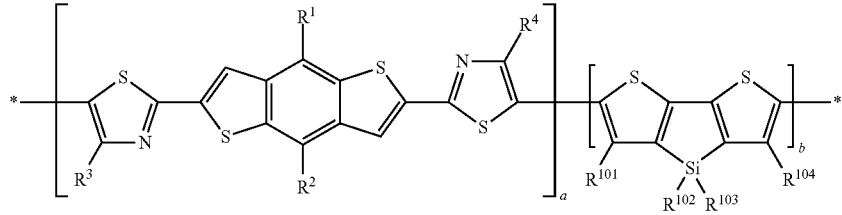 (10-8)
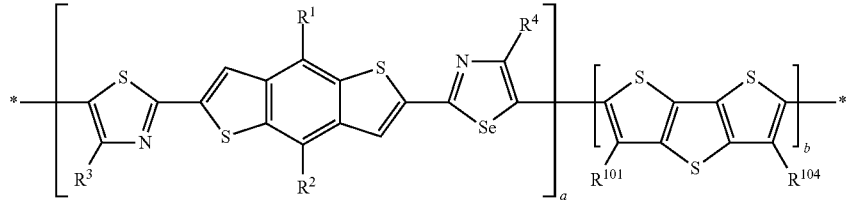 (10-9)
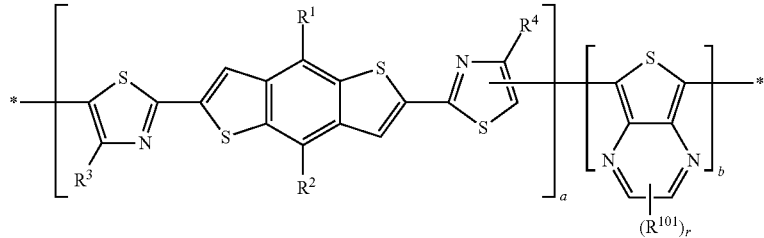 (10-10)
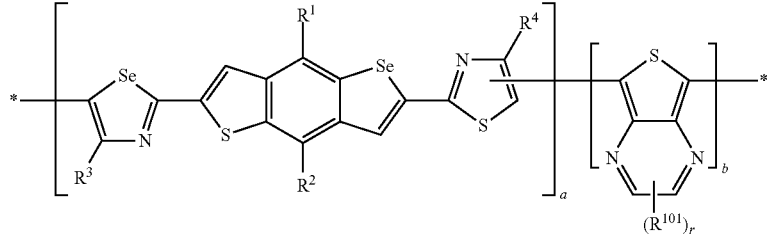 (10-11)

-continued

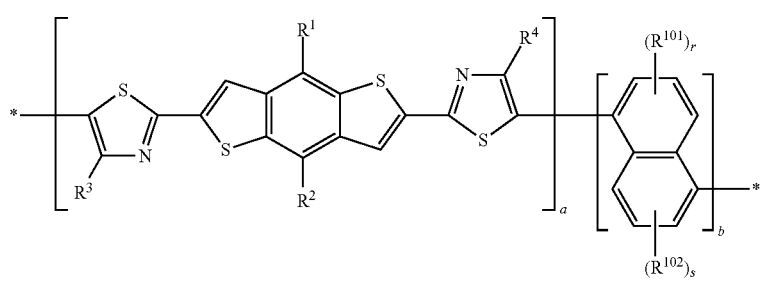
(10-12)

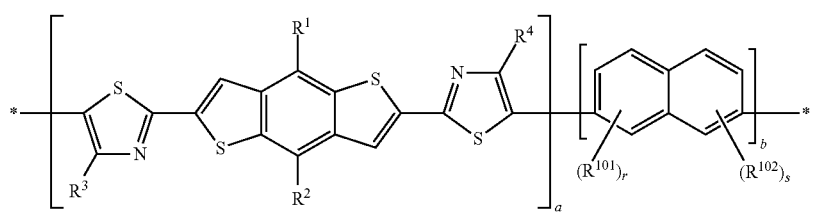
(10-13)

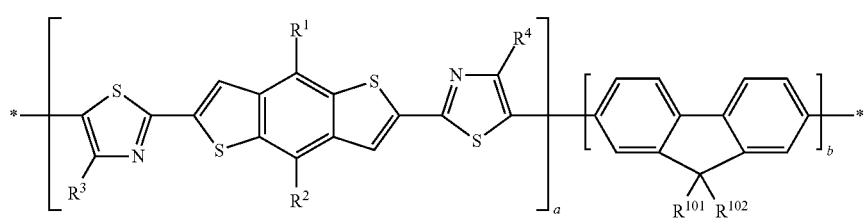
(10-14)

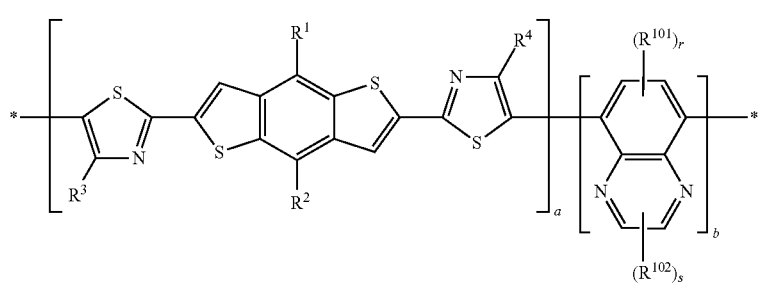
(10-15)

wherein, in Chemical Formula 10, each of $R^1$ to $R^2$ are independently selected from a halogen (—F, —Cl, —Br, or —I), a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, a substituted or unsubstituted $C_2$ to $C_{30}$ heteroaryl group, —$COR^b$ (wherein $R^b$ is selected from a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group), and —$C(=O)OR^c$ (wherein $R^c$ is selected from hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group), each of $R^3$ and $R^4$ are a combination of A and B, wherein each A is a halogen (—F, —Cl, —Br, or —I), and each B is independently selected from a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, a substituted or unsubstituted $C_2$ to $C_{30}$ heteroaryl group, —$COR^b$ (wherein $R^b$ is selected from a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to 030 heteroaryl group), and —$C(=O)OR^c$ (wherein $R^c$ is selected from hydrogen, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to $C_{30}$ arylalkyl group, and a substituted or unsubstituted $C_2$ to $C_{30}$ heteroaryl group), each of $R^{101}$ and $R^{102}$ are independently selected from hydrogen, a substituted or unsubstituted $C_4$ to $C_{20}$ aromatic ring, a substituted or unsubstituted $C_1$ to $C_{30}$ linear or branched alkyl group, a substituted or unsubstituted $C_3$ to $C_{20}$ cycloalkyl group, a substituted or unsubstituted $C_1$ to $C_{30}$ linear or branched alkoxy group, a substituted or unsubstituted $C_6$ to $C_{30}$ aryl group, a substituted or unsubstituted $C_7$ to 030 arylalkyl group, and a substituted or unsubstituted $C_2$ to $C_{30}$ heteroaryl group, each of r and s are an integer of 1 or 2, and a and b represent a mole ratio of each structural unit, wherein a ranges from about 1 mol % to about 100 mol %, and b ranges from about 0 mol % to about 99 mol %, based on a sum, 100 mol % of a and b.

7. An organic thin film comprising the organic semiconductor compound according to claim 1.

* * * * *